US010401360B2

(12) United States Patent
Escalante et al.

(10) Patent No.: US 10,401,360 B2
(45) Date of Patent: Sep. 3, 2019

(54) FLOW CYTOMETRY ASSAY METHODS

(71) Applicant: Mayo Foundation for Medical Education and Research, Rochester, MN (US)

(72) Inventors: Patricio Escalante, Rochester, MN (US); Tobias Peikert, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 317 days.

(21) Appl. No.: 14/264,286

(22) Filed: Apr. 29, 2014

(65) Prior Publication Data
US 2014/0323333 A1 Oct. 30, 2014

Related U.S. Application Data

(60) Provisional application No. 61/817,195, filed on Apr. 29, 2013.

(51) Int. Cl.
*G01N 33/53* (2006.01)
*G01N 33/569* (2006.01)
*G01N 33/50* (2006.01)

(52) U.S. Cl.
CPC ... *G01N 33/56972* (2013.01); *G01N 33/5047* (2013.01); *G01N 2333/35* (2013.01); *G01N 2333/7051* (2013.01); *G01N 2333/70514* (2013.01); *G01N 2333/70517* (2013.01); *G01N 2333/70596* (2013.01); *G01N 2800/60* (2013.01)

(58) Field of Classification Search
CPC ......... G01N 33/56972; G01N 33/5047; G01N 2333/7051; G01N 2333/70514; G01N 2333/70596; G01N 2333/35; G01N 2333/70517; G01N 2800/60
See application file for complete search history.

(56) References Cited

U.S. PATENT DOCUMENTS

| | | | |
|---|---|---|---|
| 4,208,479 A | 6/1980 | Zuk | |
| 7,572,597 B2 | 8/2009 | Lalvani et al. | |
| 7,575,870 B1 | 8/2009 | Lalvani et al. | |
| 7,608,392 B2 | 10/2009 | Rothel et al. | |
| 7,785,607 B2 | 8/2010 | Goletti et al. | |
| 8,030,005 B2 | 10/2011 | Kelleher et al. | |
| 2005/0074822 A1 | 4/2005 | Nixon | |
| 2009/0221005 A1 | 9/2009 | Kelleher et al. | |
| 2015/0010927 A1 | 1/2015 | Escalante et al. | |

FOREIGN PATENT DOCUMENTS

WO WO 2011/113953 9/2011

OTHER PUBLICATIONS

Ravn et al., (The Journal of Infectious Diseases 1999;179:637-45).*
Smith et al (Infection and Immunity, 2000, p. 7144-7148).*
Escalante 2015, American Journal of Respiratory and Critical Care Medicine vol. 192,No. 5, p. 605.*
Final Office Action in U.S. Appl. No. 14/371,371, dated Mar. 28, 2016, 18 pages.
Arend et al., "Antigenic equivalence of human T-cell responses to *Mycobacterium tuberculosis*-specific RD1-encoded protein antigens ESAT-6 and culture filtrate protein 10 and to mixtures of synthetic peptides," *Infect Immun.*, 68(6):3314-3321, Jun. 2000.
Berry, "An interferon-inducible neutrophil-driven blood transcriptional signature in human tuberculosis," *Nature*, 466(7309):973-977, Aug. 19, 2010.
Butera et al., "New tools for detecting latent tuberculosis infection: evaluation of RD1-specific longterm response," *BMC Infect Dis*, 9:182, Nov. 21, 2009.
Casey et al., "Enumeration of functional T-cell subsets by fluorescence-immunospot defines signatures of pathogen burden in tuberculosis," *PLoS One*, 5(12):e15619; 11 pages, Dec. 14, 2010.
Dinser et al., "Evaluation of latent tuberculosis infection in patients with inflammatory arthropathies before treatment with TNF-alpha blocking drugs using a novel flow-cytometric interferon-gamma release assay," *Rheumatology (Oxford).*, 47(2):212-218, Feb. 2008.
Einarsdottir et al., "Cytotoxicity and secretion of gamma interferon are carried out by distinct CD8 T cells during *Mycobacterium tuberculosis* infection," *Infect Immun.*, 77(10):4621-4630, Epub Aug. 10, 2009.
Escalante et al., "Evaluation of a novel flow cytometric method for the diagnosis of latent tuberculosis infection," ATS International Conference, San Francisco, May 22, 2012, 33 pages [slideshow].
Escalante et al., "Treatment effect of Isoniazid on T-cell CD25+/CD134+ co-expression in latent tuberculosis infection," Retrieved from the Internet <URL: https://www.keystonesymposia.org/index.cfm?e-Web.Account.ViewAbstractHTML%Abs . . . >.
Escalante et al., [Poster Board # B89] "Evaluation of a novel flow cytometric method for the diagnosis of latent tuberculosis infection," C61. Immunodiagnostics for Latent Tuberculosis Infection and Tuberculosis., *Am J Respir Crit Care Med.*, 185:2012:A4722, May 1, 2012.
Escalante, "Pilot study of latent tuberculosis infection with an enhanced elispot interferon-gamma release assay (TB-Elispot)," 3rd Global Symposium on IGRAs 2012 [slideshow], Retrieved from the Internet <URL: https://cme.ucsd.edu/igras/syllabus/sun/845a-Escalante-sun.pdf>, Jan. 12-15, 2012, 20 pages.
Ferrara et al., "Use in routine clinical practice of two commercial blood tests for diagnosis of infection with *Mycobacterium tuberculosis*: a prospective study," *Lancet*, 367(9519):1328-1334, Apr. 22, 2006.

(Continued)

*Primary Examiner* — Julie Wu
*Assistant Examiner* — Carmencita M Belei
(74) *Attorney, Agent, or Firm* — Fish & Richardson P.C.

(57) ABSTRACT

This document provides methods and materials involved in performing flow cytometry assay methods. For example, flow cytometry assay methods and kits are provided.

8 Claims, 24 Drawing Sheets

Specification includes a Sequence Listing.

(56) References Cited

OTHER PUBLICATIONS

Feske et al., "Enhancement of human antigen-specific memory T-cell responses by interleukin-7 may improve accuracy in diagnosing tuberculosis," *Clin Vaccine Immunol.*, 15(10):1616-1622, Epub Aug. 27, 2008.

Hsu et al., "A novel assay detecting recall response to *Mycobacterium tuberculosis*: Comparison with existing assays," *Tuberculosis* (Edinb)., 92(4):321-327, Epub Apr. 26, 2012.

Lasiglie et al., "Analysis of IL 23/IL 17 axis in patients carrying cias-1/Nalp3 gene mutation, further evidences of IL-1B influence in development of $T_H17$ cells in humans," *Eur. J. Immunol.*, p. S 596, Abstract WSC20/4, 1 page, Wednesday, Workshop, 2009.

Marin et al., "Regulatory T cell frequency and modulation of IFN-gamma and IL-17 in active and latent tuberculosis," *Tuberculosis (Edinb).*, 90(4):252-261, Epub Jul. 1, 2010.

Menzies et al., "Meta-analysis: new tests for the diagnosis of latent tuberculosis infection: areas of uncertainty and recommendations for research," *Ann Intern Med.*, 146(5):340-354, Mar. 6, 2007.

Ott et al., "CD28 costimulation enhances the sensitivity of the ELISPOT assay for detection of antigen-specific memory effector CD4 and CD8 cell populations in human diseases," *J Immunol Methods.*, 285(2):223-235, Feb. 15, 2004.

Pollock et al., "Discordant QuantiFERON-TB Gold test results among US healthcare workers with increased risk of latent tuberculosis infection: a problem or solution?" *Infect Control Hosp Epidemiol.*, 29(9):878-886, Sep. 2008.

Sester et al., "Improved efficiency in detecting cellular immunity towards *M. tuberculosis* in patients receiving immunosuppressive drug therapy," *Nephrol Dial Transplant.*, 21(11):3258-3268, Epub Aug. 25, 2006.

Sester et al., "Tuberculin skin testing underestimates a high prevalence of latent tuberculosis infection in hemodialysis patients," *Kidney Int.*, 65(5):1826-1834, May 2004.

Sutherland et al., "Pattern and diversity of cytokine production differentiates between *Mycobacterium tuberculosis* infection and disease," *Eur J Immunol*, 39(3):723-729, Mar. 2009.

Van Zyl-Smith, "Within-subject variability and boosting of T-cell interferon-gamma responses after tuberculin skin testing," *Am J Respir Crit Care Med.*, 180(1):49-58, Epub Apr. 2, 2009.

Waldrolp et al., "Normal human CD4+ memory T cells display broad heterogeneity in their activation threshold for cytokine synthesis," *J Immunol.*, 161(10):5284-5295, Nov. 15, 1998.

Watts et al., "T cell costimulatory molecules in anti-viral immunity. Potential role in immunotherapeutic vaccines," *Can J Infect Dis*, 14(4):221-229, Jul. 2003.

Zaunders et al., "High levels of human antigen-specific CD4+ T cells in peripheral blood revealed by stimulated coexpression of CD25 and CD134 (OX40)," *J Immunol.*, 183(4):2827-2836, Epub Jul. 27, 2009.

International Search Report and Written Opinion for PCT/US2013/020688, dated Apr. 11, 2013, 18 pages.

International Preliminary Report on Patentability for PCT/US2013/020688, dated Jul. 24, 2014, 6 pages.

Escalante et al., "Combinatorial Immunoprofiling in Latent Tuberculosis Infection: Toward Better Risk Stratification," *Am J Respir Crit Care Med.*, 192(5):605-617, Epub. Jun. 1, 2015.

Sadler et al., "Establishment of a healthy human range for the whole blood "OX40" assay for the detection of antigen-specific CD4+ T cells by flow cytometry," *Cytometry B Clin Cytom.*, 86(5):350-361, Epub May 14, 2014.

BD Biosciences, "ELISA and ELISPOT Reagents" [product list], Fisher Scientific [online] 2010 [retrieved on Sep. 9, 2015]. Retrieved from the Internet: <URL: https://static.fishersci.com/cmsassets/downloads/segment/Scientific/pdf/bd_elisa_elispot_product_list.pdf>, 12 pages.

BD OptEIA™, "Human IFN-g ELISA Set," [technical data sheet] BD Biosciences [online] 2010 [retrieved on Sep. 9, 2015]. Retrieved from the Internet: <URL: http://www.bdbiosciences.com/external_files/Doc_Recon_2.0/pm/tds/555142.pdf>, 2 pages.

Restrepo et al., "Tuberculosis in poorly controlled type 2 diabetes: altered cytokine expression in peripheral white blood cells," *Clin Infect Dis.*, 47(5):634-641, Sep. 1, 2008.

Van Pinxteren et al., "Diagnosis of tuberculosis based on the two specific antigens ESAT-6 and CFP10," *Clin Diagn Lab Immunol.*, 7(2):155-160, Mar. 2000.

Office Action in U.S. Appl. No. 14/371,371, dated Sep. 8, 2015, 10 pages.

Escalante et al., "Treatment effect of Isoniazid on T-cell CD25+/CD134+ co-expression in latent tuberculosis infection," keystonesymposia.org [online]. Retrieved on Apr. 17, 2013. Retrieved from the Internet <URL: https://www.keystonesymposia.org/index.cfm?e-Web.Account.ViewAbstractHTML%Abs . . . >, 1 page.

\* cited by examiner

Figure 12

(+)FACS-TB with RD1 Results (0.07% cut off)

Contingency Table

| | | FACS Double+ CD4 RD1 LTBI co0.0 | | |
|---|---|---|---|---|
| | Count / Row % | 0 | 1 | |
| Category | Normal Donor | 15 / 88.24 | 2 / 11.76 | 17 |
| | Remote TB | 1 / 50.00 | 1 / 50.00 | 2 |
| | Active TB | 0 / 0.00 | 2 / 100.00 | 2 |
| | Prob LTBI (TST+/IGRA+ or TST conv) | 0 / 0.00 | 9 / 100.00 | 9 |
| | Poss LTBI (TST+/IGRA- or TST-/IGRA+) | 3 / 100.00 | 0 / 0.00 | 3 |
| | | 19 | 14 | 33 |

(+)FACS-TB with RD1 Results (0.07% cut off)

Contingency Table

| | | FACS Double+ CD4 RD1 LTBI co0.0 | | |
|---|---|---|---|---|
| | Count / Row % | 0 | 1 | |
| TB contact likelihood | Active TB, old TB, definitive TB contact | 1 / 20.00 | 4 / 80.00 | 5 |
| | Probable TB contact | 7 / 43.75 | 9 / 56.25 | 16 |
| | Possible TB contact | 4 / 80.00 | 1 / 20.00 | 5 |
| | Unlikely TB contact | 7 / 100.00 | 0 / 0.00 | 7 |
| | | 19 | 14 | 33 |

Figure 16

Contingency Table

FACS Double+ CD4 RD1 LTBI co0.07

| Count<br>Row % | 0 | 1 | |
|---|---|---|---|
| TST-/IGRA- | 16<br>88.89 | 2<br>11.11 | 18 |
| TST+/IGRA- | 2<br>66.67 | 1<br>33.33 | 3 |
| TST+/IGRA+ | 0<br>0.00 | 10<br>100.00 | 10 |
| unk TST/IGRA- | 1<br>50.00 | 1<br>50.00 | 2 |
| | 19 | 14 | 33 |

TST / IGRA

Figure 22
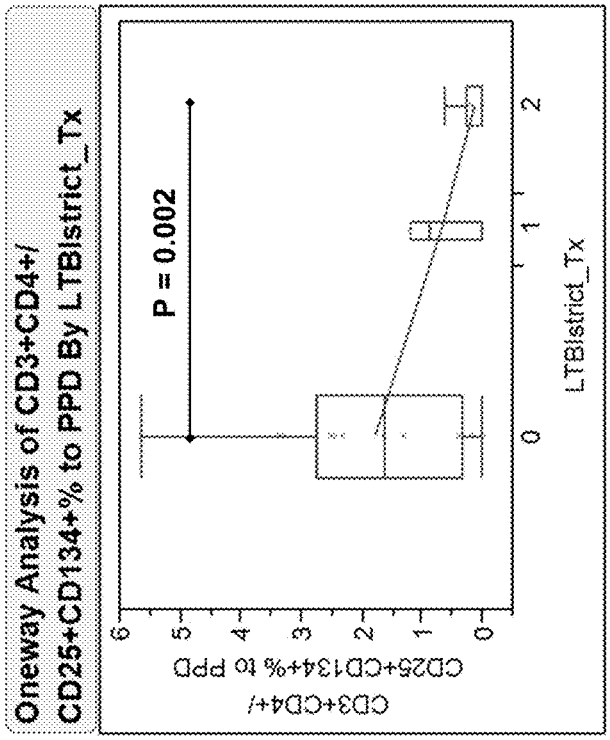
CD4+ T cells (PPD Antigen)
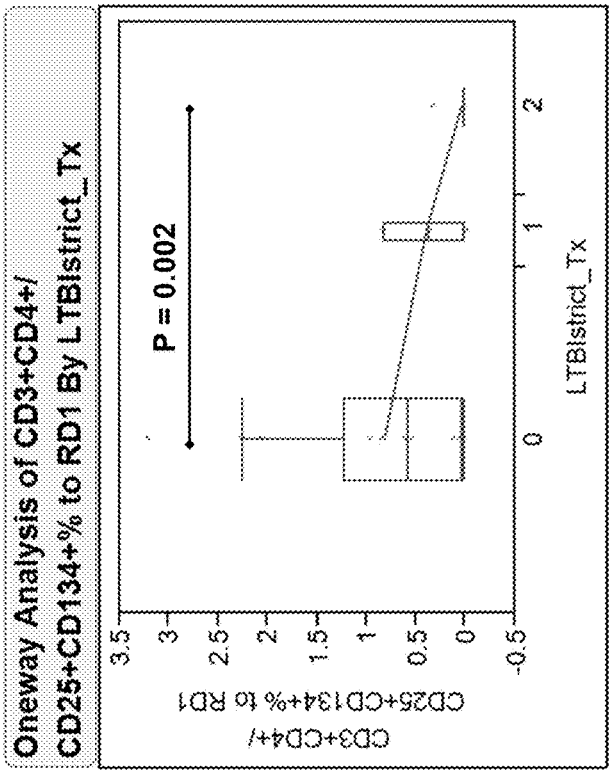
CD4+ T cells (RD1 Antigen)

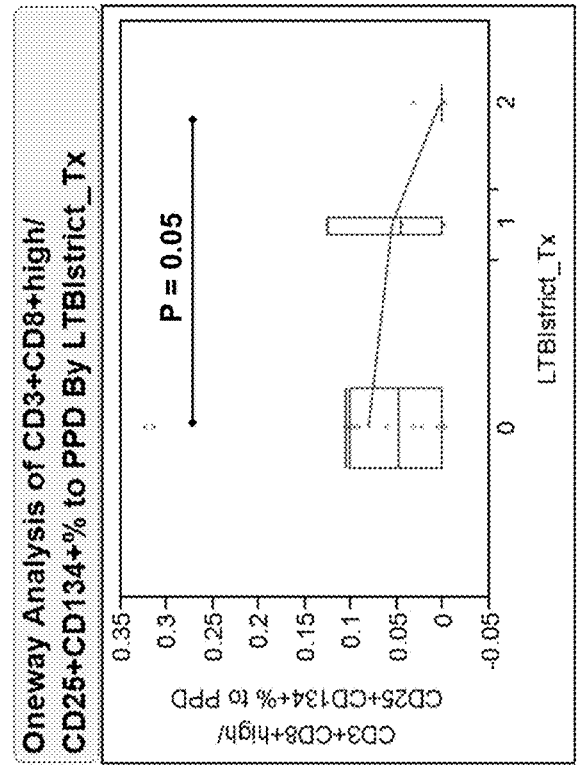
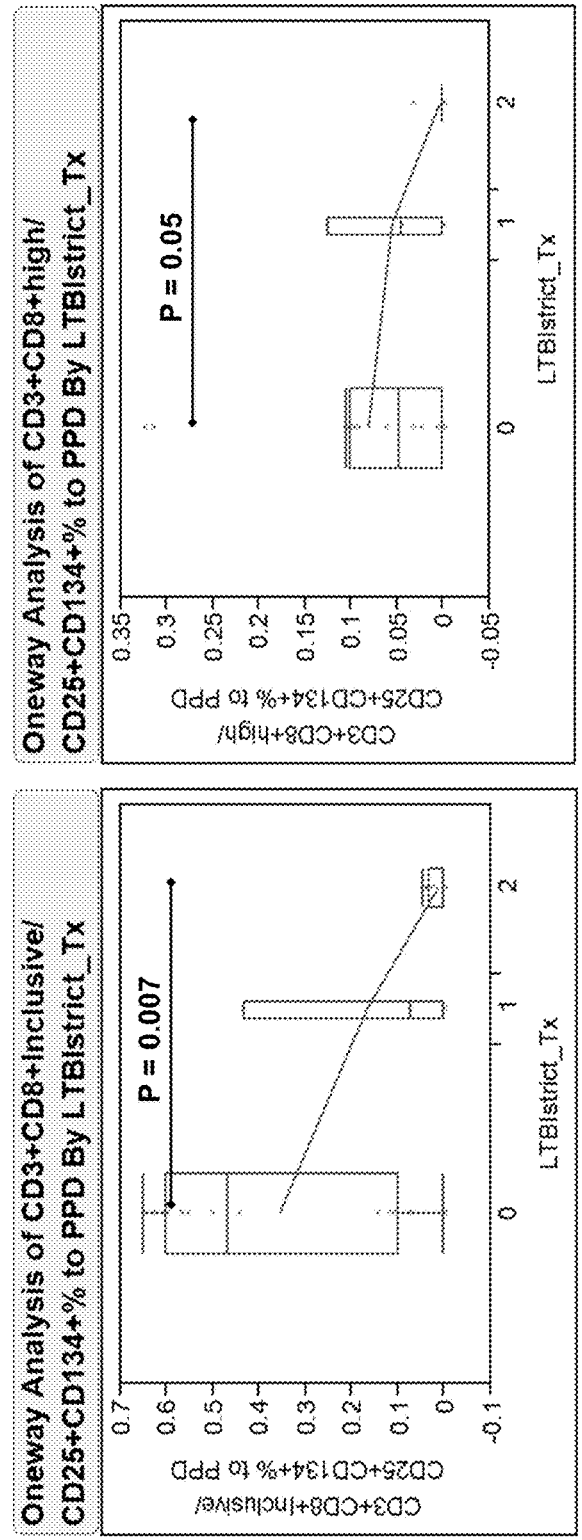
Figure 23

FLOW CYTOMETRY ASSAY METHODS

CROSS-REFERENCE TO RELATED APPLICATIONS

This application claims the benefit of U.S. Provisional Application Ser. No. 61/817,195, filed Apr. 29, 2013. The disclosure of the prior application is considered part of (and is incorporated by reference in) the disclosure of this application.

BACKGROUND

1. Technical Field

This document relates to methods and materials involved in performing flow cytometry assay methods. For example, this document relates to methods and materials for using flow cytometry assay methods to identify mammals having a latent tuberculosis infection (LTBI).

2. Background Information

Tuberculosis (TB) is important because it disproportionately affects minorities and immigrants in the United States and vast populations around the world. Accurate detection of LTBI continues to be challenging, and undiagnosed LTBI patients can progress to active TB disease with potentially devastating consequences. Interpretation of discordant testing (e.g., tuberculin skin tests (TST) and interferon-gamma release assays (IGRA) in LTBI also can be a significant problem. Both TST and IGRA tests usually detect T-cell activation against *Mycobacterium tuberculosis* (MTB), but they do not appear to differentiate patients with dormant forms of TB infection from the ones who have cleared their infections.

SUMMARY

This document provides methods and materials involved in performing flow cytometry assay methods. For example, this document provides flow cytometry assay methods and kits. In some cases, the methods and kits provided herein can be used to identify mammals having a LTBI.

As described herein, flow cytometry assay methods and kits can be designed to determine the percentage and/or number of $CD3^-CD8^+/CD25^+/CD134^-$ cells present within a sample, the percentage and/or number of $(CD3^+)CD8^+/CD25^+/CD134^+$ cells present within a sample, and/or the percentage and/or number of $(CD3^+)CD4^+/CD25^+/CD134^+$ cells present within a sample. The flow cytometry assay methods and kits provided herein can identify highly likely LTBIs and subjects with prior exposure to TB that are falsely identified as being negative or falsely identified as being positive with commercial assays such as QUANTIFERON TB GOLD IN-TUBE™ (Cellestis, Australia) and/or the tuberculin skin test (TST). The flow cytometry assay methods and kits provided herein can also identify likely LTBIs that have a substantial risk of TB reactivation ("reactivatable LTBI").

Having the ability to identify humans with a LTBI as described herein can allow clinicians and other medical personnel to identify patients in need of TB treatment in an accurate and efficient manner. In addition, the methods and materials provided herein can help the medical community better target TB prevention strategies to those areas with cases of LTBIs identified as described herein. In some cases, the methods and materials provided herein can be used to assist a qualified clinician and/or healthcare provider in determining whether or not a mammal has a latent tuberculosis infection with or without substantial risk of TB reactivation.

In one aspect, this document features a flow cytometry assay method. The method can include (a) obtaining a sample comprising human cells, (b) exposing the human cells to an *M. tuberculosis* antigen preparation to obtain a stimulated human cell preparation, (c) contacting the stimulated human cell preparation with a fluorescently labeled anti-CD8 antibody, a fluorescently labeled anti-CD25 antibody, and a fluorescently labeled anti-CD134 antibody to obtain a labeled cell preparation, and (d) introducing the labeled cell preparation into a flow cytometer to determine the percentage of $CD8^+/CD25^+/CD134^+$ cells present within the labeled cell preparation. The human cells can be human cells from a human having had a previous tuberculin skin test– (TST–) negative or interferon-gamma release assay– (IGRA–) negative test result. The human cells can be human cells from a human having had previous TST-negative and IGRA-negative test results. The human cells can be human cells from a human having had a previous TST-positive or IGRA-positive test result. The human cells can be human cells from a human having had a previous TST-positive and IGRA-positive test result. The human cells can be freshly obtained human cells, or can be frozen human cells. The human cells can be human peripheral blood mononuclear cells (PBMCs). The *M. tuberculosis* antigen preparation can include a polypeptide selected from the group consisting of $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides. The *M. tuberculosis* antigen preparation can contain $ESAT-6_{1-20}$, $ESAT-6_{31-50}$, $ESAT-6_{42-65}$, $HAT-6_{61-80}$, $CFP-10_{51-70}$, and $CFP-10_{71-90}$ polypeptides. The method can include contacting the stimulated human cell preparation with a fluorescently labeled anti-CD4 antibody. The percentage of $CD4^+/CD25^+/CD134^+$ cells present within the labeled cell preparation can be determined.

In another aspect, this document features a flow cytometry assay method. The method can include (a) obtaining a sample comprising human cells, (b) exposing the human cells to an *M. tuberculosis* antigen preparation to obtain a stimulated human cell preparation, (c) contacting the stimulated human cell preparation with a fluorescently labeled anti-CD3 antibody, a fluorescently labeled anti-CD8 antibody, a fluorescently labeled anti-CD25 antibody, and a fluorescently labeled anti-CD134 antibody to obtain a labeled cell preparation, and (d) introducing the labeled cell preparation into a flow cytometer to determine the percentage of $CD3^+/CD8^+/CD25^+/CD134^-$ cells present within the labeled cell preparation. The human cells can be human cells from a human having had a previous TST-negative or IGRA-negative test result. The human cells can be human cells from a human having had previous TST-negative and IGRA-negative test results. The human cells can be human cells from a human having had a previous TST-positive or IGRA-positive test result. The human cells can be human cells from a human having had previous TST-positive and IGRA-positive test results. The human cells can be freshly obtained human cells, or can be frozen human cells. The human cells can be human PBMCs. The *M. tuberculosis* antigen preparation can include a polypeptide selected from the group consisting of $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides. The *M. tuberculosis* antigen preparation can contain $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides. The method can include contacting the stimulated human cell preparation with a fluorescently labeled anti-CD4 antibody. The percentage of CD3+/CD4+/CD25+/CD134+ cells present within the labeled cell preparation can be determined.

In another aspect, this document features a kit containing a *M. tuberculosis* antigen preparation, a fluorescently labeled anti-CD8 antibody, a fluorescently labeled anti-CD25 antibody, and a fluorescently labeled anti-CD134 antibody. The *M. tuberculosis* antigen preparation can include a polypeptide selected from the group consisting of ESAT-6$_{1-20}$, ESAT-6$_{31-50}$, ESAT-6$_{42-65}$, ESAT-6$_{61-80}$, CFP-10$_{51-70}$, and CFP-10$_{71-90}$ polypeptides. The *M. tuberculosis* antigen preparation can contain ESAT-6$_{1-20}$, ESAT-6$_{31-50}$, ESAT-6$_{42-65}$, HAT-6$_{61-80}$, CFP-10$_{51-70}$, and CFP-10$_{71-90}$ polypeptides. The kit can include a fluorescently labeled anti-CD4 antibody, or a fluorescently labeled anti-CD3 antibody.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 12 provides a summary of FACS-TB (RD1) results in CD4$^+$ T-cells by category and TB contact likelihood.

FIG. 16 contains a table of FACS-TB (RD1) results in CD4$^+$ T-cells by TST/IGRA status.

FIG. 22 contains graphs demonstrating the effect of isoniazid treatment on FACS-TB with RD1 peptides in CD4+ and FACS-TB with PPD in CD4+ T-cells in LTBI cases. Patients had a history of untreated LTBI ("0"; N=14), partially treated LTBI ("1"; N=3) or treated LTBI ("2"; N=7).

FIG. 23 contains graphs demonstrating the effect of isoniazid treatment on FACS-TB with PPD antigen in CD8+ (inclusive (high and low gate) and high gate) T-cells in LTBI cases. Patients had a history of untreated LTBI ("0"; N=14), partially treated LTBI ("1"; N=3), or treated LTBI ("2"; N=7).

DETAILED DESCRIPTION

Figure 1:
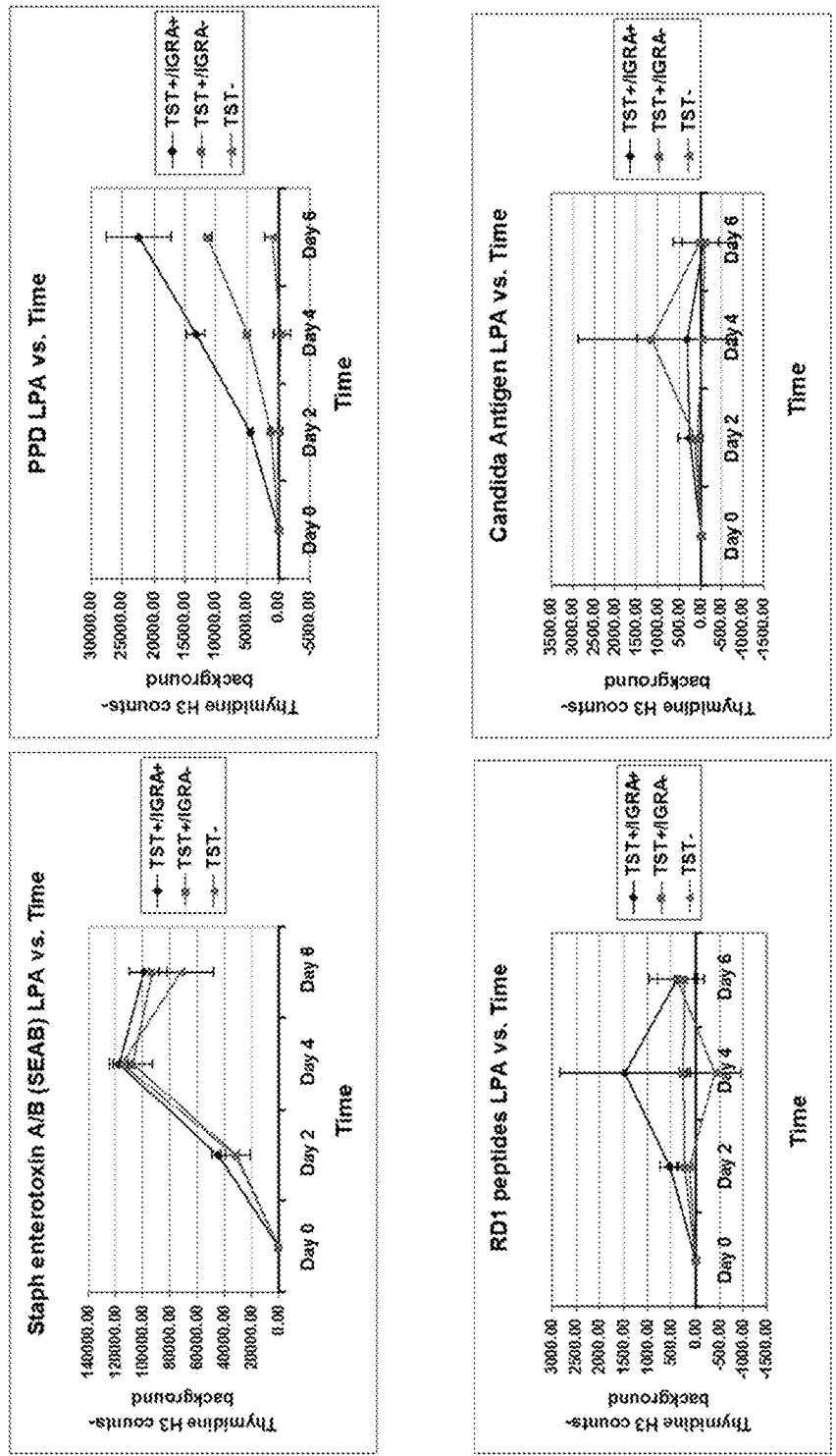
FIG. 1 contains graphs plotting the lymphocyte proliferation assay (LPA) over time for cells from subjects with prior TST$^-$ results, prior TST$^+$/IGRA$^+$ results, or prior TST$^+$/IGRA$^-$ results exposed to the indicated antigens.

This document provides methods and materials involved in performing flow cytometry assay methods. For example, this document provides flow cytometry assay methods and kits. In some cases, the methods and kits provided herein can be used to identify mammals (e.g., humans) having a LTBI.

A flow cytometry assay method provided herein can include incubating cells (e.g., PBMCs or cells from a whole blood sample) with a stimulation preparation. The cells can be freshly obtained cells or cells that have been stored or frozen. The stimulation preparation can include a mixture of ESAT-6 and CFP-10 polypeptides (RD1 peptide antigen). For example, a stimulation preparation can include a mixture of $ESAT-6_{1-20}$, $ESAT-6_{31-50}$, $ESAT-6_{42-65}$, $HAT-6_{61-80}$, $CFP-10_{51-70}$, and $CFP-10_{71-90}$ polypeptides. In some cases, a stimulation preparation can include a combination of an anti-CD28 antibody and an anti-CD49d antibody. Any appropriate length of time can be used for the incubation period. For example, the cells can be incubated as 37° C. for between 25 and 90 hours (e.g., between 25 and 86 hours, between 25 and 60 hours, or between 35 and 45 hours).

Once the cells are treated with the stimulation preparation, they can be stained with fluorescently labeled antibodies. For example, the cells of a stimulated cell preparation can be stained with fluorescently labeled anti-CD3 antibodies, fluorescently labeled anti-CD4 antibodies, fluorescently labeled anti-CD8 antibodies, fluorescently labeled anti-CD25 antibodies, fluorescently labeled anti-CD134 antibodies, or a combination thereof (e.g., a combination of fluorescently labeled anti-CD8 antibodies, fluorescently labeled anti-CD25 antibodies, and fluorescently labeled anti-CD134 antibodies). In some cases, the methods provided herein can be performed using unstimulated cells.

Once stained, the cells of the preparation can be subjected to flow cytometry to determine the percentage of $CD3^-CD8^+/CD25^+/CD134^-$ cells present within a sample, the percentage of $(CD3^+)CD8^+/CD25^+/CD134^+$ cells present within a sample, and/or the percentage of $(CD3^+)CD4^+/CD25^+/CD134^+$. In some cases, the number of $CD3^-CD8^+/CD25^+/CD134^-$ cells, $(CD3^+)CD8^+/CD25^+/CD134^+$ cells, and/or $(CD3^+)CD4^+/CD25^+/CD134^+$ cells per a fixed number of cells (e.g., about $2\times10^5$ cells) can be determined. In some cases, the percentage of $CD8^+/CD25^+/CD134^-$ cells present within a sample, the percentage of $CD8^+/CD25^+/CD134^+$ cells present within a sample, the percentage of $CD4^+/CD25^+/CD134^+$, the number of $CD8^+/CD25^+/CD134^-$ cells per a fixed number of cells, $CD8^+/CD25^+/CD134^+$ cells per a fixed number of cells, and/or $CD4^+/CD25^+/CD134^+$ cells per a fixed number of cells can be used to determine if a mammal has a LTBI. In some cases, a percentage of $(CD3^+)CD8^+/CD25^+/CD134^+$ of antigen-specific activated cells present within a sample that is greater than 0.12% (RD1 antigen minus nil) and/or 0.11% (PPD antigen minus nil) can indicate that the mammal has a LTBI with reactivation potential. In some cases, a percentage of $(CD3^+)CD4^+/CD25^+/CD134^+$ of antigen-specific activated cells present within a sample that is greater than 0.002% (RD1 antigen minus nil) and 0.39% (PPD antigen minus nil) can indicate that the mammal has a LTBI with reactivation potential. In some cases, a percentage of (CD3+)CD4+ CD25+/CD134+ of antigen-specific activated cells present within a sample that is greater than 0.04% (RD1 antigen minus nil) and 0.39% (PPD antigen minus nil) can indicate that the mammal has a LTBI with reactivation potential. In some cases, a number of $CD3^-CD8^+/CD25^+/CD134^-$ of antigen-specific activated cells greater than 6 (RD1 antigen minus nil) and/or 27 (PPD antigen minus nil) per $2\times10^5$ cells can indicate that the mammal has had an exposure to TB without an apparent adaptive T-cell response to TB. In some cases, a number of $(CD3^+)CD8^+/CD25^+/CD134^+$ of antigen-specific activated cells greater than 9 (PPD antigen minus nil) per $2\times10^5$ cells can indicate that the mammal has a LTBI with reactivation potential. In some cases, a number of $(CD3^+)CD4^+/CD25^+/CD134^+$ of antigen-specific activated cells greater than 10 (RD1 antigen minus nil) and/or 70 (PPD antigen minus nil) per $2\times10^5$ cells can indicate that the mammal has a LTBI with reactivation potential.

In some cases, background counts such as the number of $(CD3^+)CD4^+$ (or $CD8^+)CD25^+/CD134^+$ cells found in unstimulated samples (nil or media without antigen(s)) can be subtracted prior to assessing whether or not a mammal has a LTBI. For example, a number of $(CD3^+)CD8^+/CD25^+/CD134^+$ of antigen-specific activated cells greater than 8 (RD1 antigen minus nil) and/or 9 (PPD antigen minus nil) per $2\times10^5$ cells can indicate that the mammal has a LTBI with reactivation potential. Likewise, a number of $(CD3^+)CD4^+/CD25^+/CD134^+$ of antigen-specific activated cells greater than 10 (RD1 antigen minus nil) and/or 70 (PPD antigen minus nil) per $2\times10^5$ cells can indicate that the mammal has a LTBI with reactivation potential.

This document also provides kits for performing a flow cytometry assay method provided herein. For example, reagents of a stimulation preparation and reagents for assessing cells for expression of CD3, CD4, CD8, CD25, and/or CD134 can be combined as an article of manufacture such as a kit. In one embodiment, a kit can contain an *M. tuberculosis* antigen preparation such as a mixture of ESAT-6 and CFP-10 polypeptides for stimulating cells and fluorescently labeled anti-CD3 antibodies, fluorescently labeled anti-CD4 antibodies, fluorescently labeled anti-CD8 antibodies, fluorescently labeled anti-CD25 antibodies, fluorescently labeled anti-CD134 antibodies, or a combination thereof (e.g., a combination of fluorescently labeled anti-CD8 antibodies, fluorescently labeled anti-CD25 antibodies, and fluorescently labeled anti-CD134 antibodies). In some case, a kit provided herein can include an anti-CD28 antibody and/or an anti-CD49d antibody in addition to an *M. tuberculosis* antigen preparation and control samples for stimulating cells and unstimulated cells.

In some cases, a kit can contain buffers, positive control samples, or combinations thereof. The reagents within a kit can be housed together in various combinations or can be packaged in separate vials or containers within a larger package. The kits provided herein also can include labels or packaging inserts setting out instructions for preparation and use. For example, a kit can contain a packaging insert describing that an elevated level of $CD8^+/CD25^+/CD134^+$ cells can support a diagnosis of LTBI.

The invention will be further described in the following examples, which do not limit the scope of the invention described in the claims.

EXAMPLES

Example 1—Evaluation of a Flow Cytometric Method for the Diagnosis of Latent Tuberculosis Infection The following was performed to evaluate the diagnostic performance of a FACS assay for the detection of T-cell $CD25^+CD134^+$ co-expression (FACS-TB) in healthy subjects and suspected LTBI cases. A prospective comparison of the diagnostic characteristics of FACS-TB using peripheral blood mononuclear cells (PBMCs) samples from subjects unlikely to have LTBI (low probability of previous TB contact and both negative TST and commercial IGRA) and likely to have LTBI (high probability of TB contact and/or both TST+/IGRA+ tests) was performed. PBMCs were stimulated with specific (RD1-peptides) and non-specific (PPD) MTB antigens as well as controls, stained with fluorescent dye-conjugated anti-CD4, anti-CD25, and anti-OX40 (anti-CD134) antibodies, and $2\times10^5$ cells were analyzed by FACS (BD FACSCanto™). The area under the receiver characteristic (ROC) curve (AUC) were analyzed, and various cut-offs to best differentiate these populations were tested.

The FACS-TB assay protocol was developed to detect LTBIs. The following steps 1 and 2 were performed on day 1, and the following steps 3 through 11 were performed on day 3.

1. Prepare cell culture media: Use a conical tube; add 50 mL RPMI 1640 (with 2 mM L-glutamine) supplemented with 10% human AB serum and 0.5 mL of Pen-Strep mixture (Gibco #15140-122) to final concentration of penicillin 100 IU/mL and streptomycin (100 µg/mL) in culture medium.

2. Within 2 hours of blood collection in heparinized tubes (total 20 cc or less for fresh whole blood), harvest peripheral blood monocytes (PBMC) using a density gradient centrifugation of whole blood (Ficoll-Plaque™ technique), wash cells two times with PBS and add cell culture media in a polypropylene sterile tube for a final concentration $2.5\times10^6$ PBMCs/mL. Harvest cells can be used directly in assay or freeze using RPMI with 10% DMSO and 12% Human Sera Albumin or FBS. Immediately after putting cells in cryovials, put in the freezer at −80° C. and/or liquid nitrogen. Frozen cell pellets can be sent in mail package with dry ice for subsequent laboratory processing after thawing.

3. Perform stimulation procedures with PBMC's using concentration of (a) *Staphylococcus* Enterotoxin A and B (SEAB) or other super antigen or mitogen (e.g., phytohemagglutinin (PHA), anti-CD3 monoclonal antibodies), (b) tuberculin PPD™ (Staten Serum Institute, Denmark), (c) RD1-peptide mix (ESAT-6 and CFP-10 peptides mix), or (d) *Candida* protein mix. An unstimulated sample is used as a control. Four ESAT-6 polypeptides and two CFP-10 polypeptides are included in the RD1-peptide mix. The ESAT-6 polypeptides are $ESAT-6_{1-20}$ (MTEQQWNF-AGIEAAASAIQG; SEQ ID NO:1), $ESAT-6_{31-50}$ (EGKQS-LTKLAAAWGGSGSEA; SEQ ID NO:2), $ESAT-6_{42-65}$ (AWGGSGSEAY-QGVQQKWDATATEL; SEQ ID NO:3), and $ESAT-6_{61-80}$ (TATELNNALQNLARTIS-EAG SEQ ID NO:4). The CFP-10 polypeptides are $CFP-10_{51-70}$ (AQAAV-VRFQEA-ANKQKQELD; SEQ ID NO:5) and $CFP-10_{71-90}$ (EISTNIRQAGVQYSRADEEQ; SEQ ID NO:6).

4. Keep 2.5 mL of blood sample for whole blood experiments using the following antigen stimulation conditions and controls.

5. Stimulation procedure (under the hood):
   a. Tube 1 (SEAB to final concentration at 2 ng/mL w/v—same final concentration as per PMBC's stimulation conditions):
      i. Dilute 24 µL of freshly thawed SEAB stock (0.5 ng/µL) and in 476 µL of culture media.
      ii. Then add 3 mL of diluted fresh SEAB to 3 mL of whole blood from Sodium heparin sample to tube 1 (total of 3 mL).
   b. Tube 2 (PPD final concentration of 20 µg/mL—same final concentration as per PMBCs stimulation conditions):
      i. Tube 2: "PPD": Add 60 µL of PPD in 1.44 mL of culture media.
      ii. Then add 1.5 mL of diluted PPD and 1.5 mL of whole blood from Sodium heparin sample to tube 2 ("PPD at 20 µg/mL") (3 mL total).
   c. Tube 3 (CFP-10+ESAT-6 peptide mix same final concentrations per PMBC's stimulation conditions):
      i. Tube 3: "CFP-10 (add at 4 µg/mL)/ESAT-6 mix (add at 2 µg/mL)": all stock is 1 µg/µL. Add 12 µL of CFP10 and add 6 µL of ESAT-6 with 1.49 mL of culture media.
      ii. Add 1.5 mL of diluted fresh CFP-10/ESAT-6 in culture media at 1.5 mL of whole blood from sodium heparin sample to tube: (3 mL total).
   d. Tube 4 (*Candida* activated same final concentration as per PMBC's stimulation conditions):
      i. Dilute 3 µL of *Candida* stock solution (10 µg/µL) in 1.5 mL of culture media ("*Candida* to 10 µg/mL in culture media").
      ii. Then add 1.5 mL of diluted *Candida* and 1.5 mL of whole blood from Sodium heparin sample to tube (3 mL total).

6. Tube 5 ("unstimulated blood"):
   a. Use 1.5 mL of whole blood from Sodium heparin sample for tube 5, then add 1.5 mL of culture medium to dilute 1:1.

7. Add 5 µL of anti-CD28/anti-CD49d reagent (Becton Dickinson FastImmune™ CD28/CD49d Costimulatory Reagent; BD Biosciences cat#347690) to activated tubes (Tubes 2, 3, 4, and 5) and vortex gently.

8. Incubate all tubes in a $CO_2$ incubator at 37° C. for about 40 hours.

9. Incubated tubes are stained with fluorescent dye-conjugated anti-CD3, anti-CD4 (or antiCD8), anti-CD25, and anti-OX40 (anti-CD134) antibodies, and 2×10⁵ cells were analyzed by FACS (BD FACSCanto™).

Figure 2:
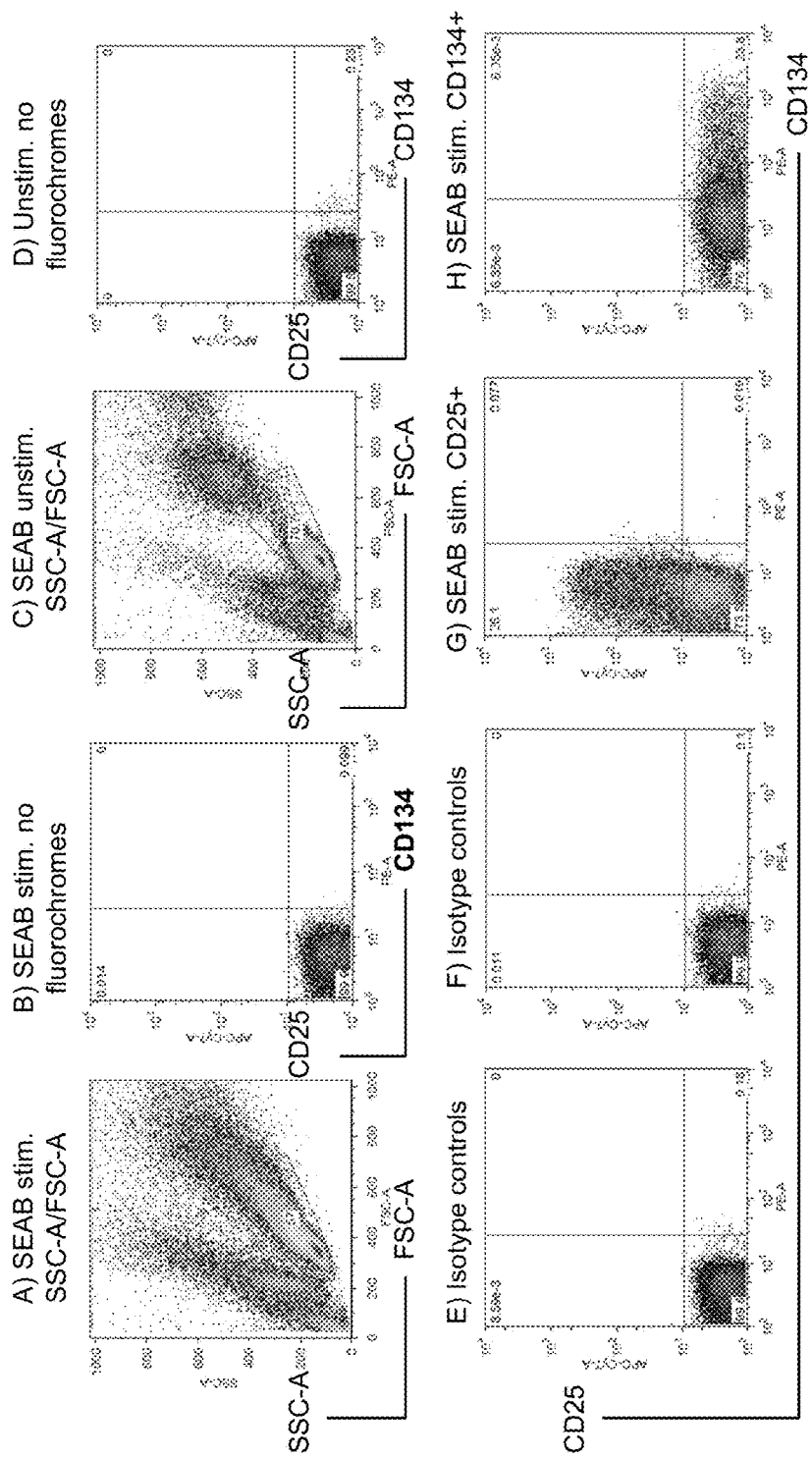
FIGS. 2A-2H contain examples of FACS-TB gating of quadrants for CD3$^+$CD4$^+$/CD25$^+$/CD134$^+$ T-cell subsets (right upper quadrant box in B and D-H) and controls. A-D) Viable lymphocyte gating strategy using side and forward scatter plots in PBMC stimulated with Staphylococcal enterotoxin A and B (SEAB) (A-B), and unstimulated sample (C-D); E-F) Isotype controls in SEAB-stimulated (E) and unstimulated samples (F); G) Single anti-CD25$^+$ fluorochrome staining in SEAB-stimulated sample; H) Single anti-CD134$^+$ fluorochrome staining in SEAB-stimulated sample.

10. Set FACS-TB gating of quadrants for CD3⁺CD4⁺ (or CD8⁺)/CD25⁺/CD134⁺ T-cell subsets (Please see example in FIG. 2) and controls by using FloJow™ or similar software. Gate for viable lymphocytes by using side and forward scatter plots in PBMC stimulated with Staphylococcal enterotoxin A and B (SEAB), and unstimulated sample. Gate upper right quadrant quadrants for CD3⁺CD4⁺/CD25⁺/CD134⁺ T-cell subsets by using isotype controls in SEAB-stimulated and unstimulated samples. Confirm quadrants for CD3⁺CD4⁺/CD25⁺/CD134⁺ T-cell subsets by gating a single anti-CD25⁺ fluorochrome staining in a SEAB-stimulated sample, and a single anti-CD134⁺ fluorochrome staining in a SEAB-stimulated sample.

Figure 3:
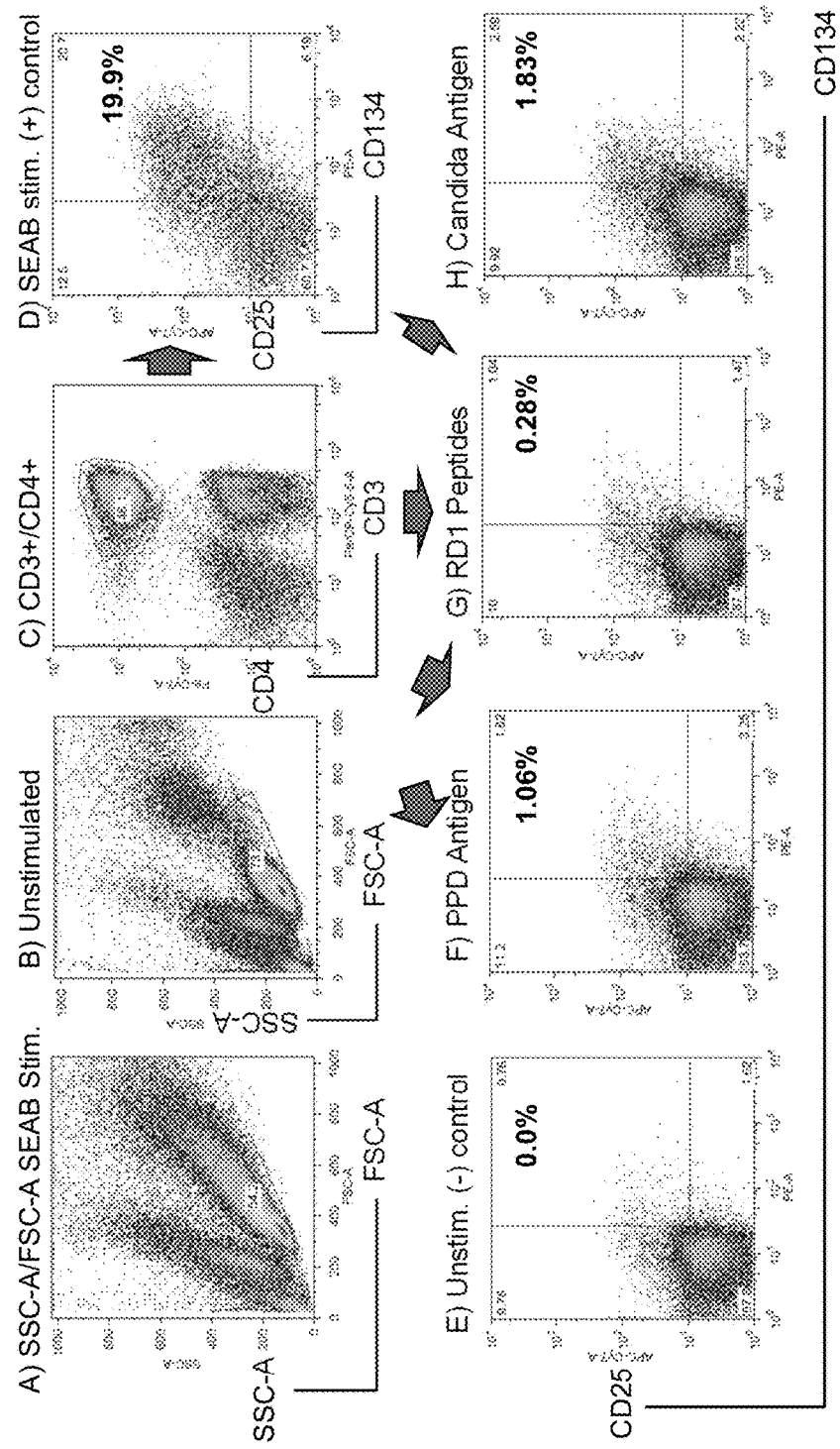
FIGS. 3A-3H contain examples of FACS-TB test (% CD25$^+$CD134$^+$) gating strategy in activated T-cells (CD3$^+$ CD4$^+$) in a suspected LTBI case (prior TST$^+$/IGRA$^+$ results). Only CD4$^+$ T cells are shown (CD3$^+$/CD4$^+$ gated). A-B) Viable lymphocyte gate using side and forward scatter plots in SEAB-stimulated (A) and unstimulated (B) samples; C) Gate on CD3$^+$/CD4$^+$; D) % CD3$^+$CD4$^+$/CD25$^+$CD134$^+$ co-expression (right upper quadrant box) after 48 hours incubation with SEAB (non-specific T-cell activator; positive control); E) Unstimulated sample; F) PPD (non-specific MTB antigen); G) ESAT-6/CFP-10 peptide mixture (specific MTB antigen of RD1 (region of difference) peptide antigens); H) *Candida* (antigen-specific T-cell activator; positive control). Percentages indicate the calculated distribution of CD25+ CD134+ among CD3+CD4+ T cells after the subtraction of background (nil).
Figure 4:
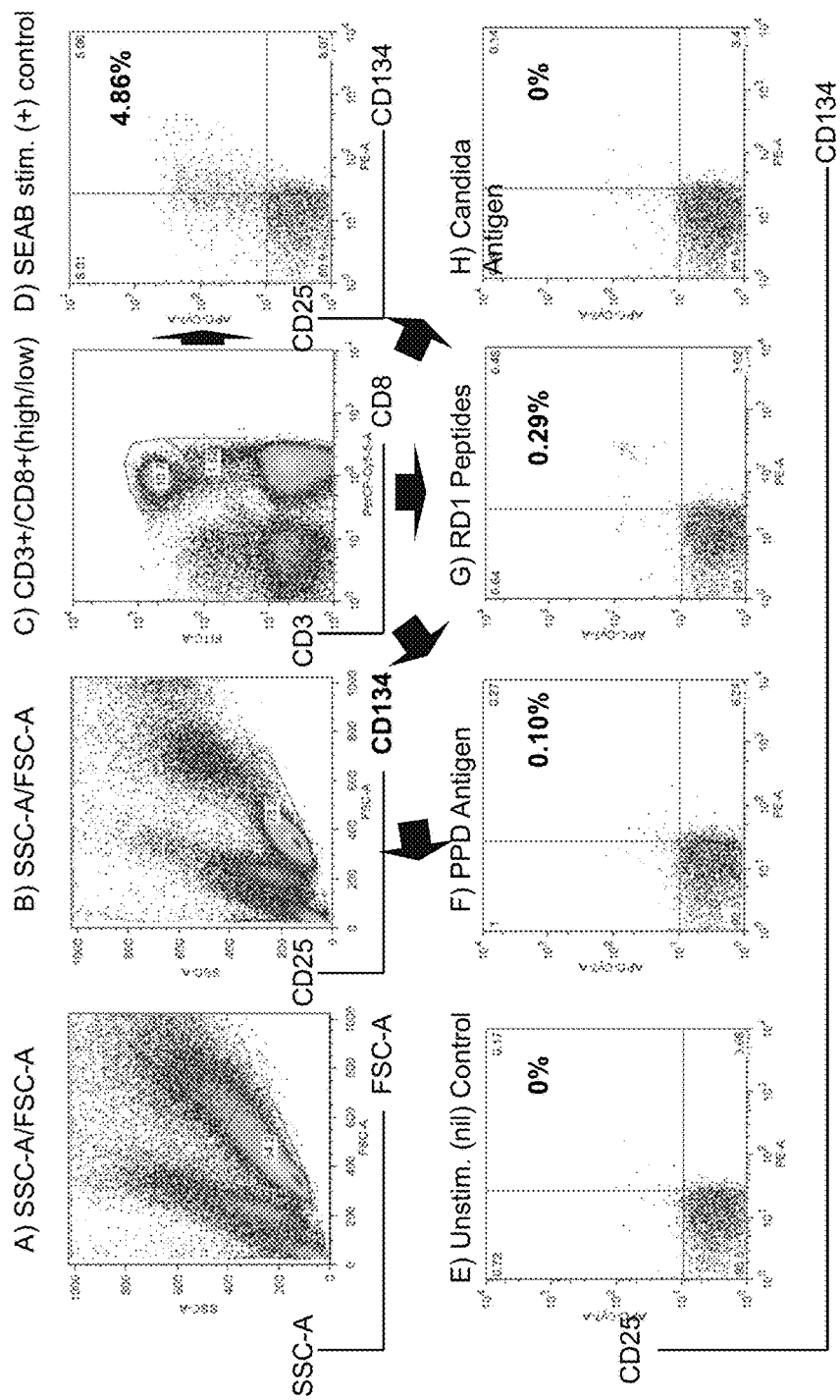
FIGS. 4A-4H contain examples of FACS-TB test (% CD25+CD134+) gating strategy in activated T-cells (CD3+/CD8+) in a suspected LTBI case (prior TST+/IGRA+ results). Only CD8+ T cells (CD8+ high and CD8+low) are shown (CD3+/CD8+ gated). A-B) Viable lymphocyte gate using side and forward scatter plots in SEAB-stimulated and unstimulated samples; C) Gate on CD3+/CD8+(high) and CD3+/CD8+(low); D) % CD3+/CD8+(high and low)/CD25+CD134+ co-expression (right upper quadrant box) after 48 hours incubation with SEAB (non-specific T-cell activator; positive control); E) Unstimulated sample; F) PPD (non-specific MTB antigen); G) ESAT-6/CFP-10 peptide mixture (specific MTB antigen of RD1 peptide antigens); H) *Candida* (antigen-specific T-cell activator; positive control). Percentages (bold) indicate the calculated distribution of CD25+ CD134+ among CD3+/CD8+ T cells after the subtraction of background (nil).
Figure 5:
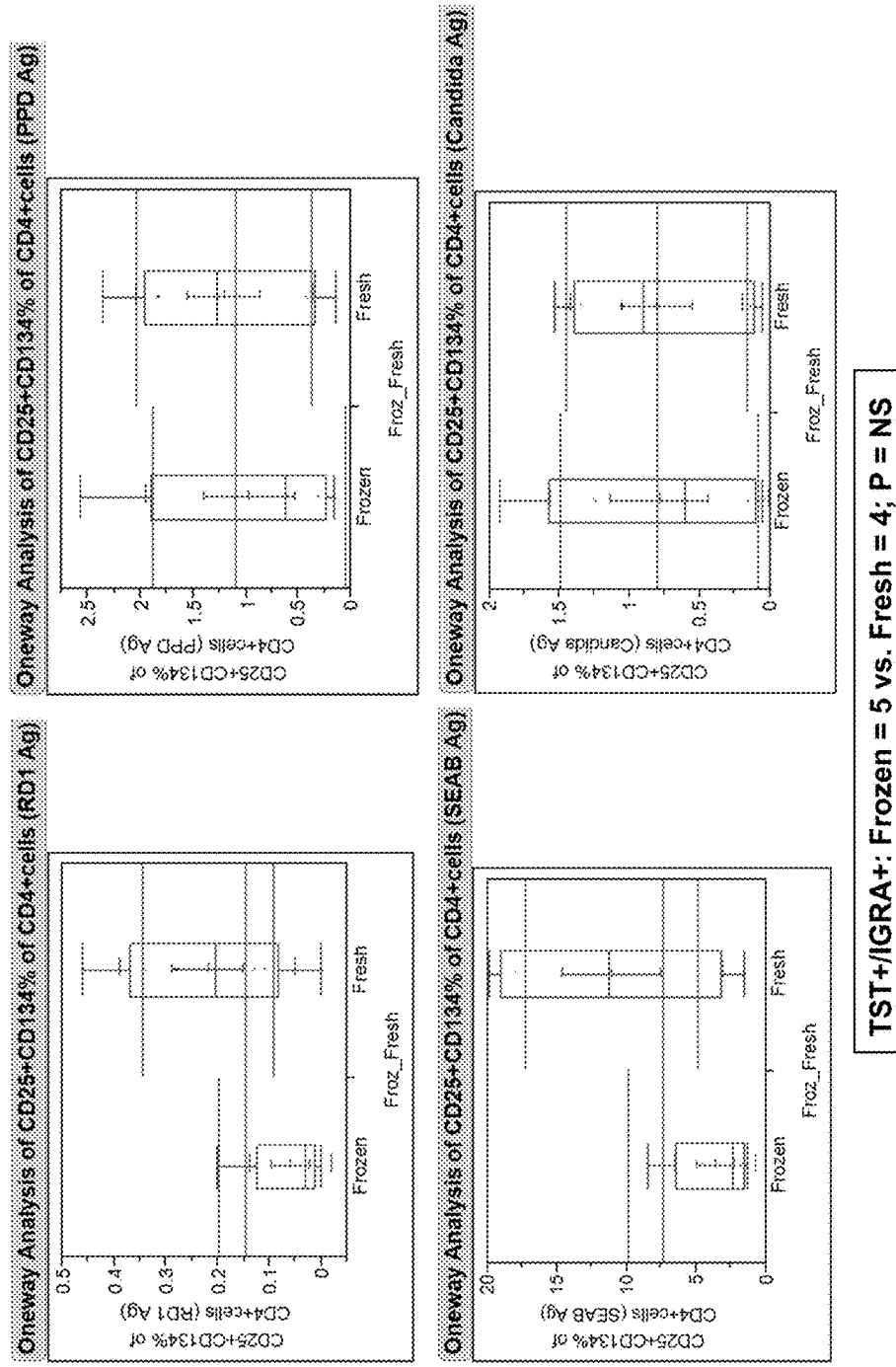
FIG. 5 contains graphs demonstrating FACS-TB reproducibility and comparison between results using fresh and frozen peripheral blood mononuclear cell samples for the indicated antigens.
Figure 6:
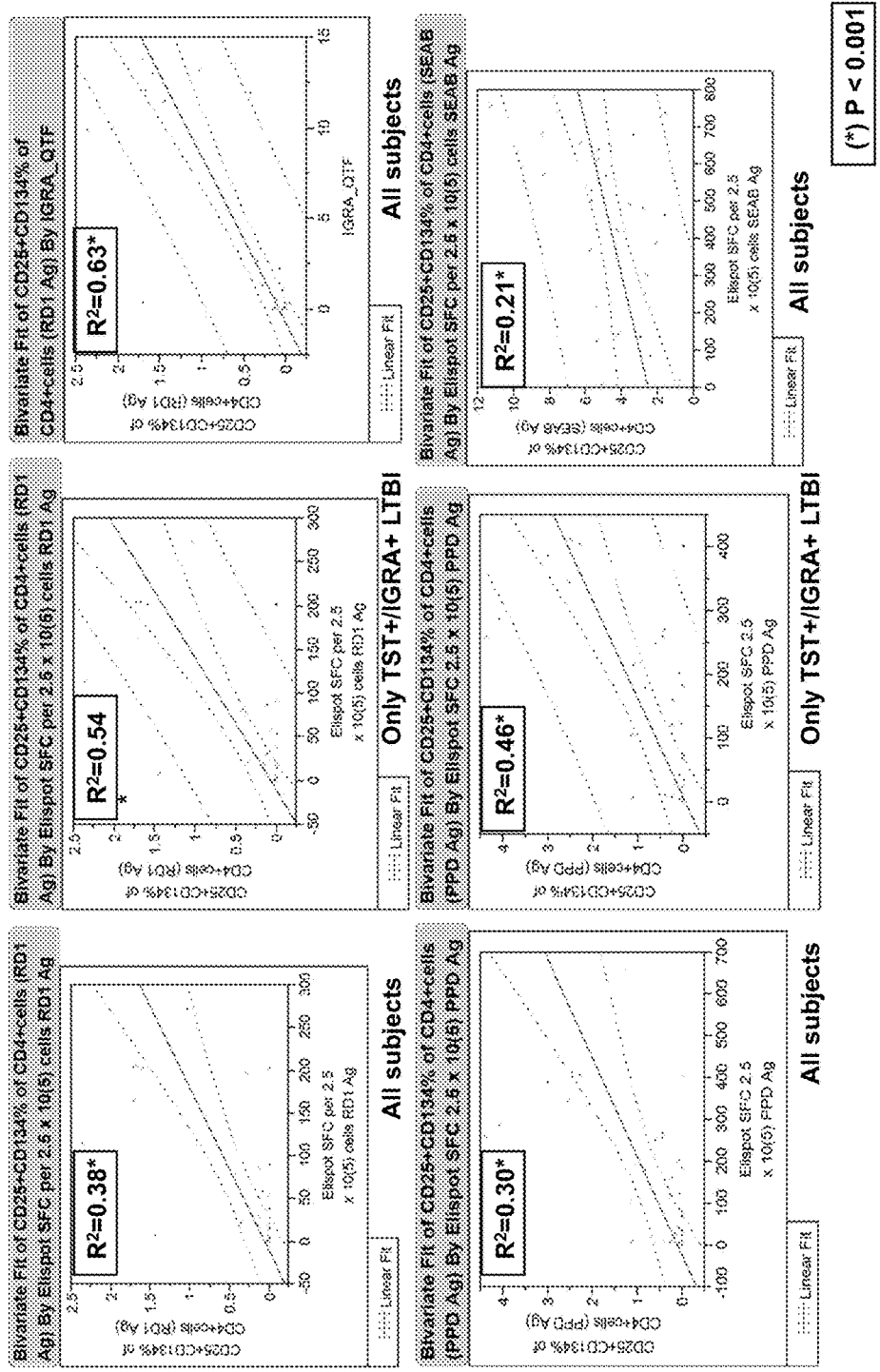
FIG. 6 contains graphs demonstrating FACS-TB testing correlations.
Figure 7:
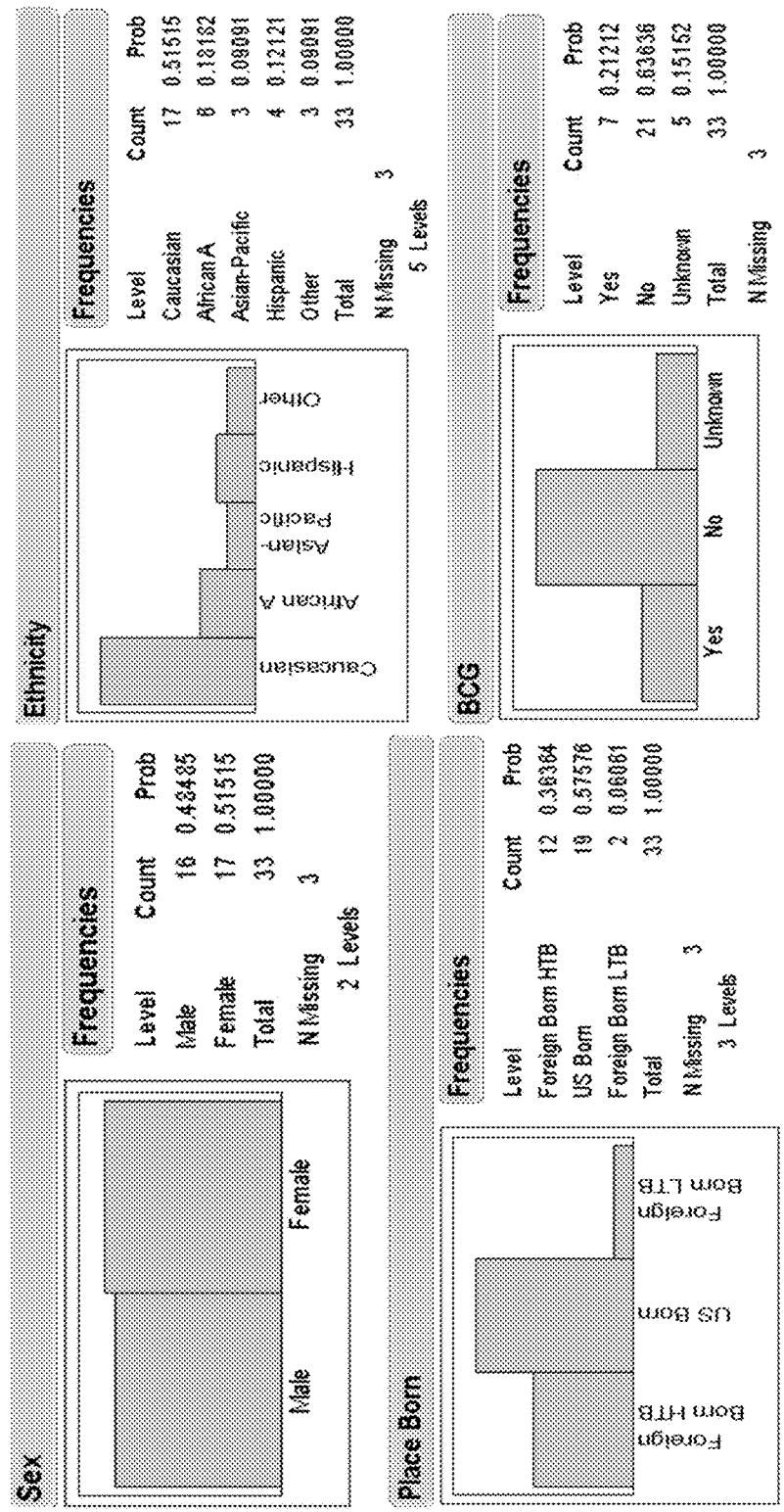
FIG. 7 provides characteristics of the study population (N=33). Foreign HTB=foreign subject born in a high TB prevalence area; LTB=foreign subject born in a low TB prevalence area.
Figure 8:
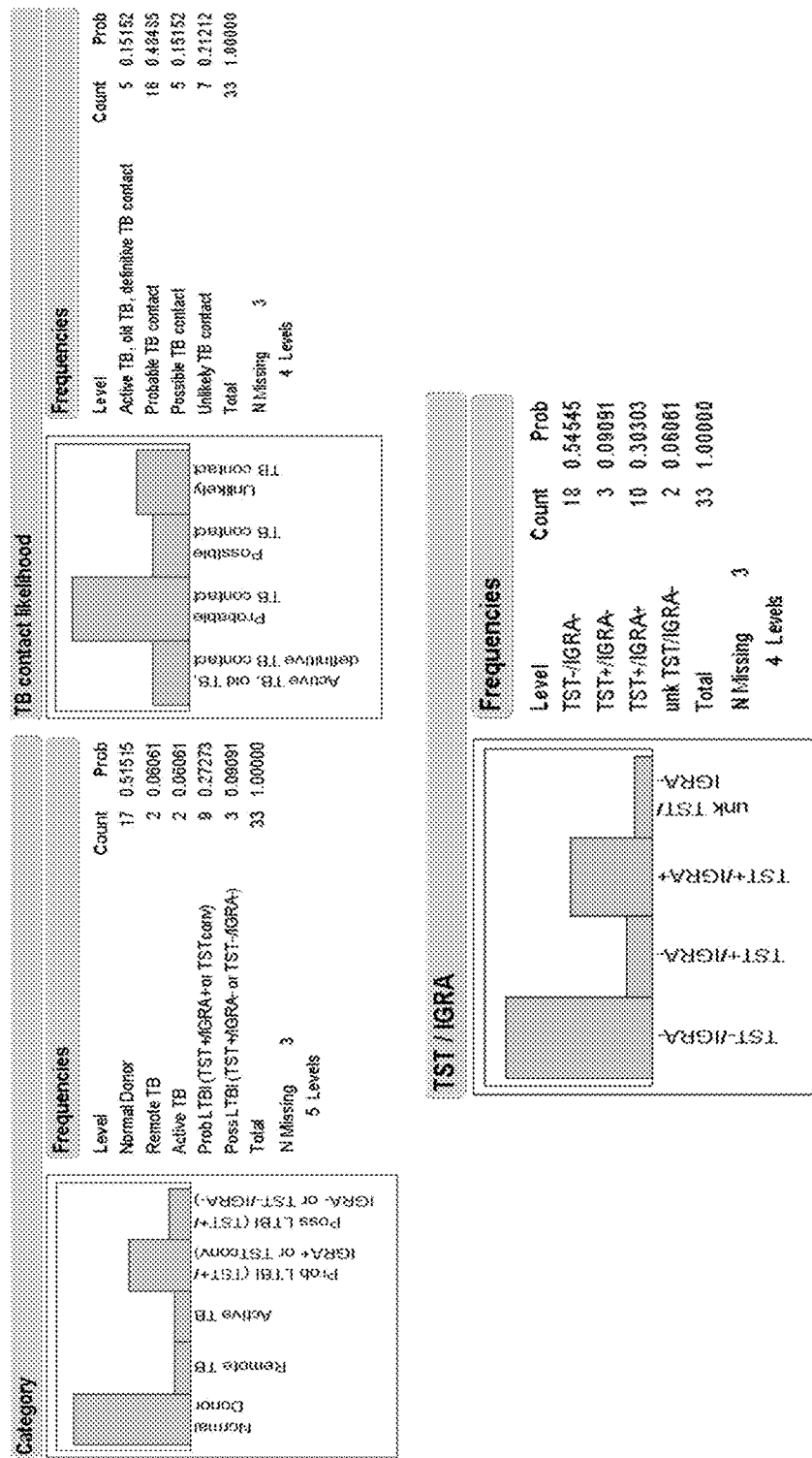
FIG. 8 provides clinical characteristics of the study population (N=33).
Figure 9:
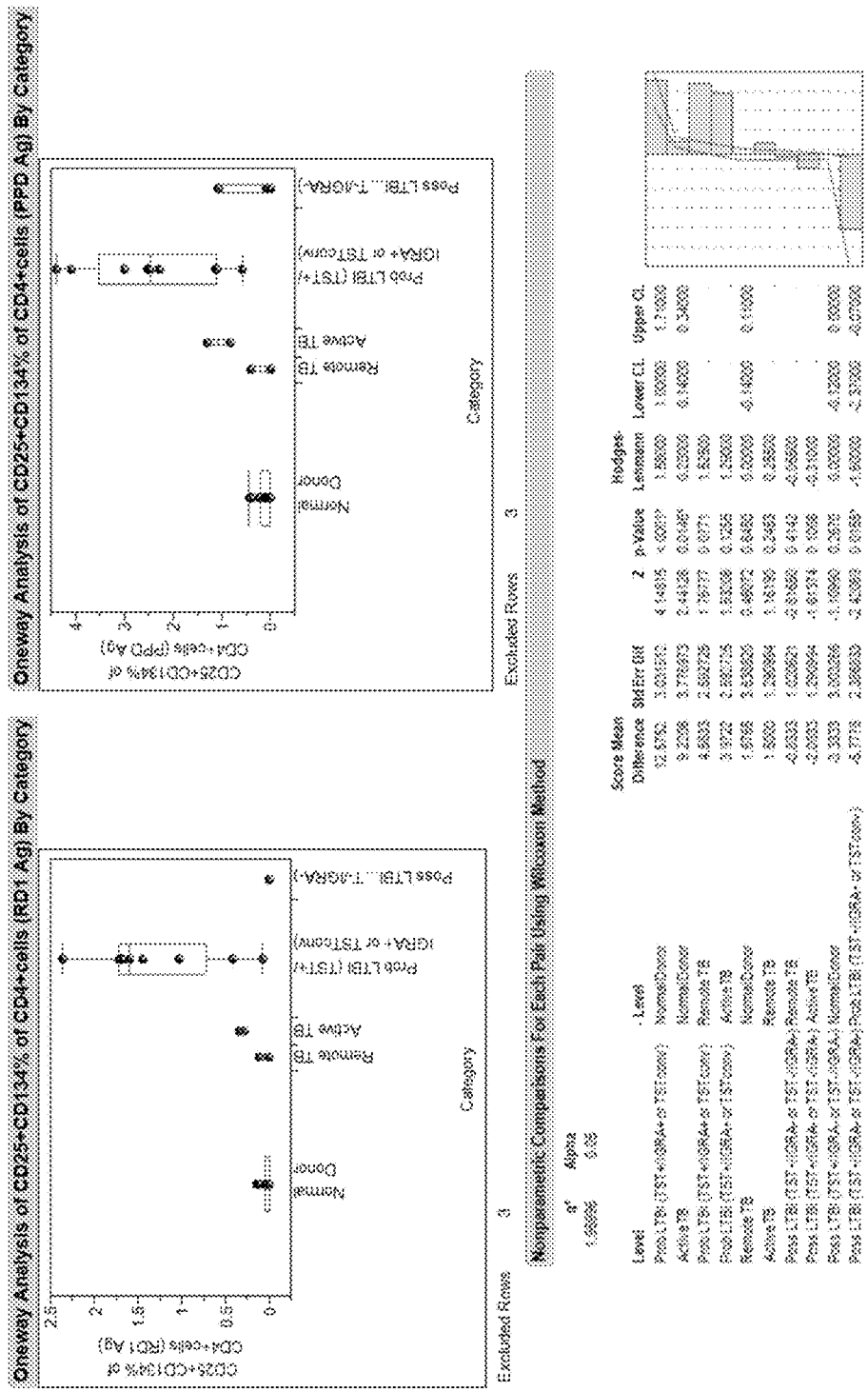
FIG. 9 provides data for FACS-TB (RD1 and PPD) in CD4$^+$ T-cells by category, including nonparametric statistical comparisons for each pair using a Wilcoxon method (CD3$^+$CD4$^+$ T-cells activated by RD1 peptide antigens).
Figure 10:
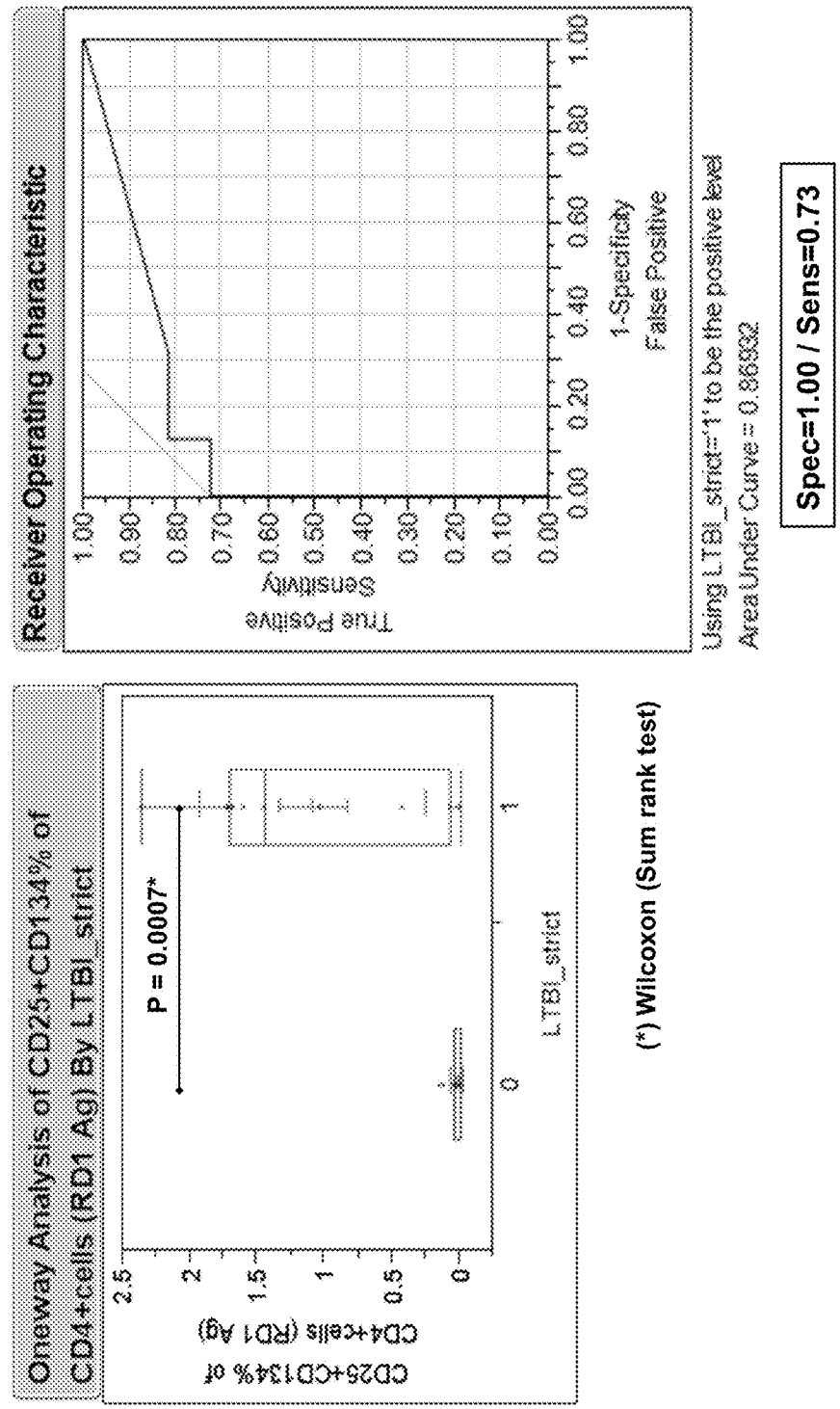
FIG. 10 contains graphs of FACS-TB (RD1) results in CD4$^+$ T-cells for healthy donors vs. LTBI cases ("Spec"=specificity; "Sens"=sensitivity).
Figure 11:
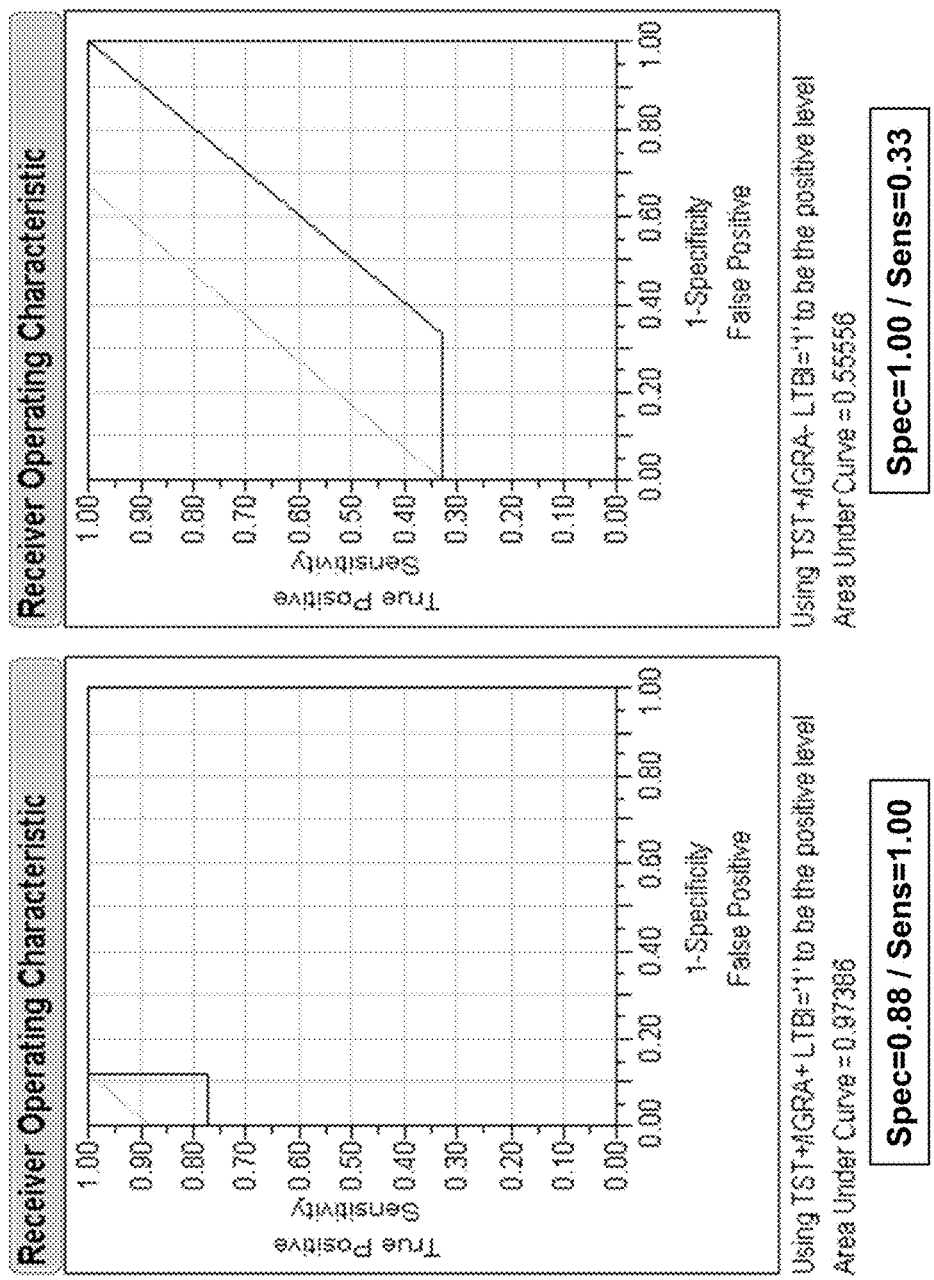
FIG. 11 contains graphs of FACS-TB (RD1) results in CD4$^+$ T-cells for donors vs. TST+/IGRA+ (left panel) and TST+/IGRA− (right panel) cases.
Figure 13:
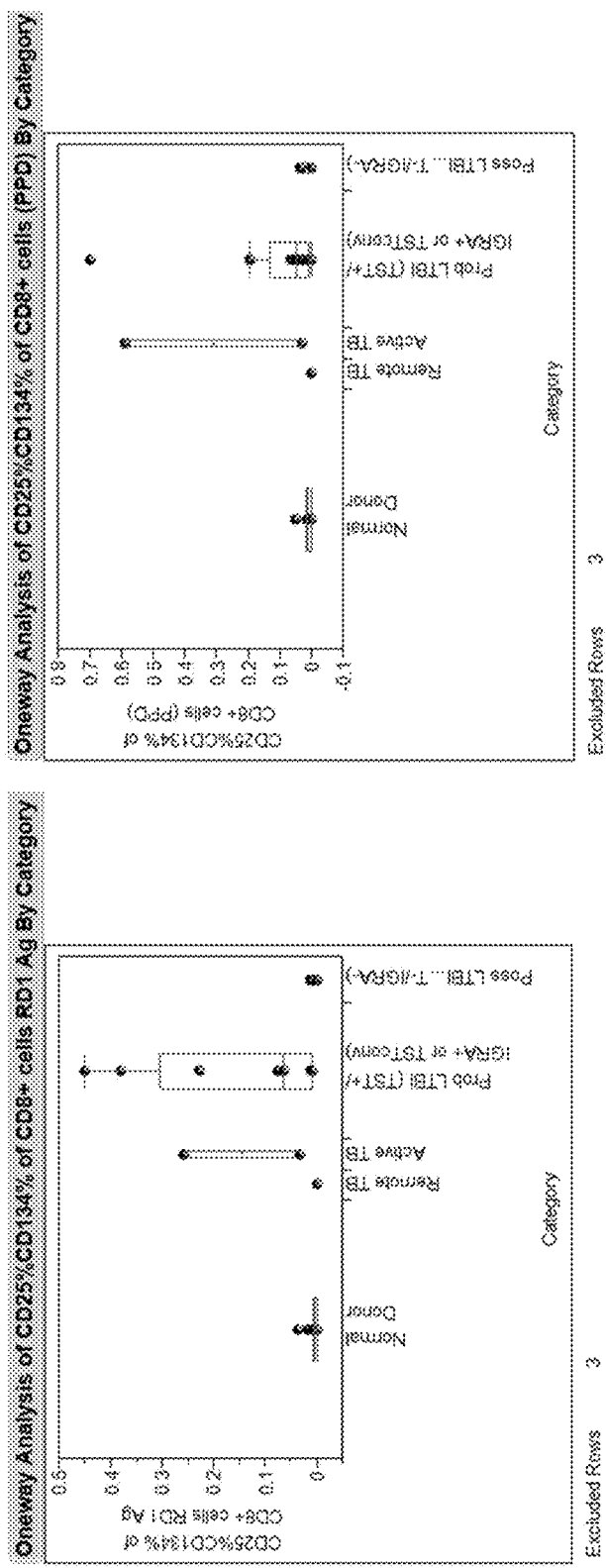
FIG. 13 contains graphs of FACS-TB results in CD8$^+$ T-cells (RD1 vs. PPD) by category.
Figure 14:
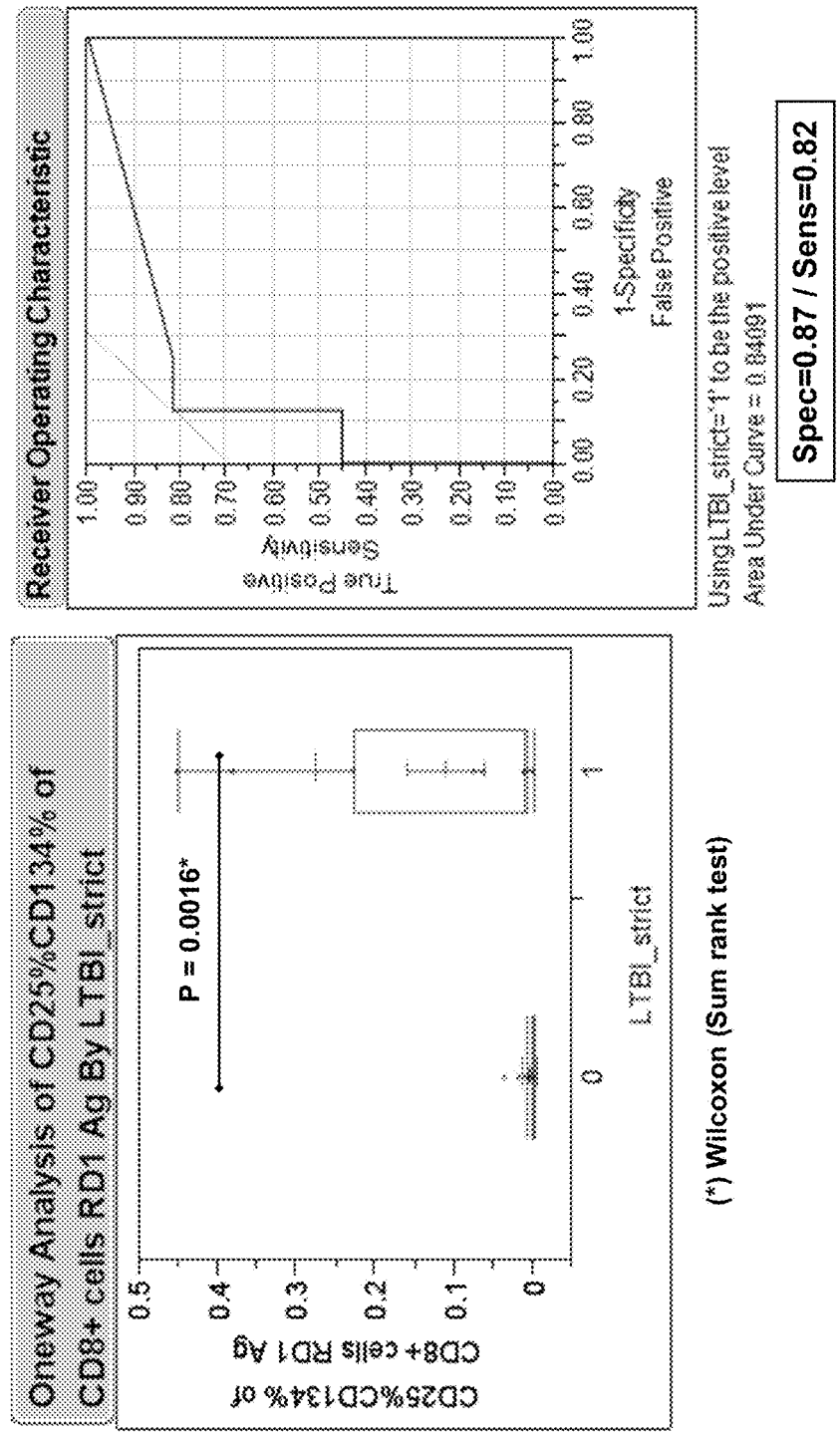
FIG. 14 contains graphs of FACS-TB (RD1) results in CD8$^+$ T-cells for healthy donors vs. LTBI cases.
Figure 15:
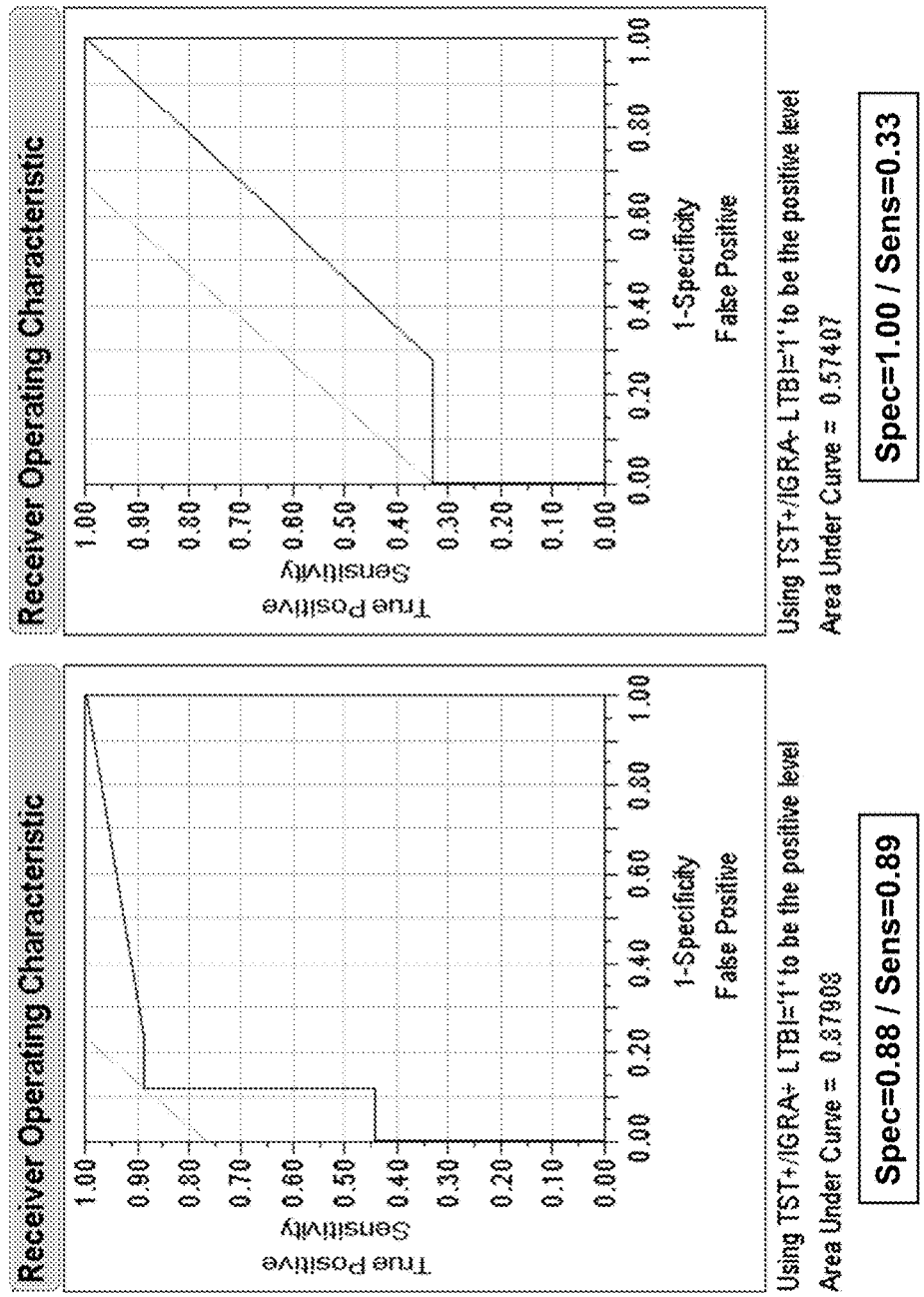
FIG. 15 contains graphs of FACS-TB (RD1) results in CD8$^+$ T-cells for donors vs. TST+/IGRA+ and TST+/IGRA− cases.
Figure 17:
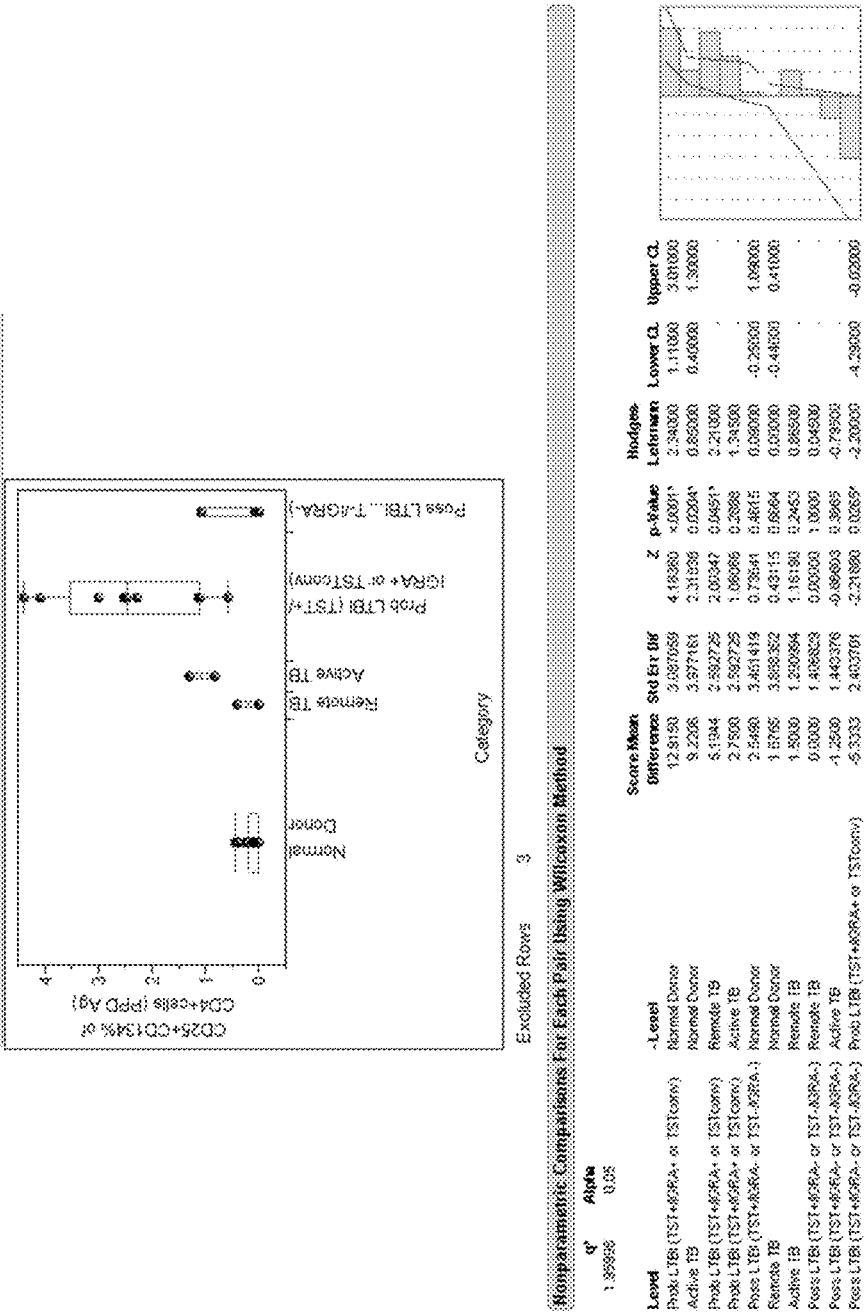
FIG. 17 provides a summary of FACS-TB (PPD) results in CD4$^+$ T-cells by category.
Figure 18:
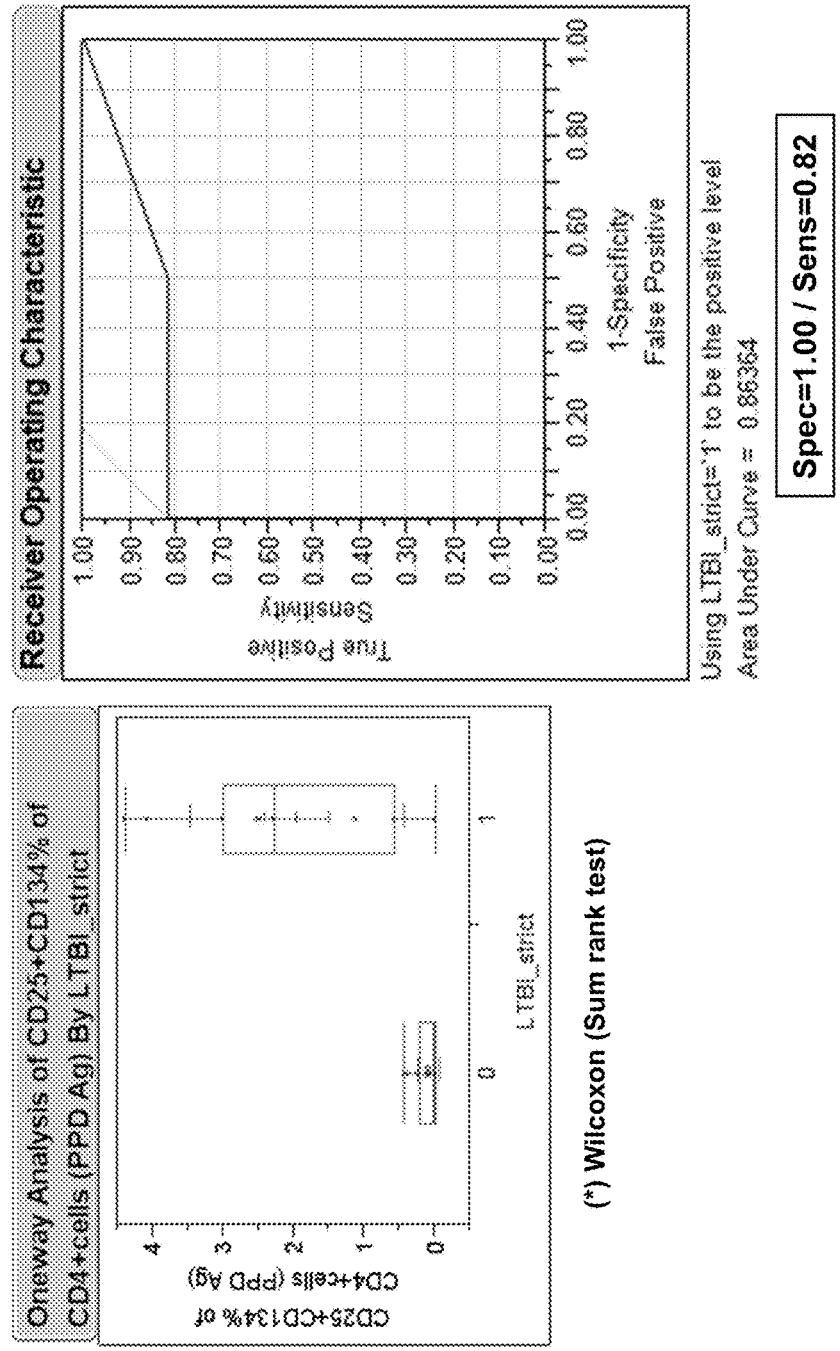
FIG. 18 provides a summary of FACS-TB (PPD) results in CD4$^+$ T-cells from healthy donors vs. LTBI cases, including nonparametric statistical comparisons for each pair using a Wilcoxon method (CD3$^+$CD4$^+$ T-cells activated by PPD antigen).
Figure 19:
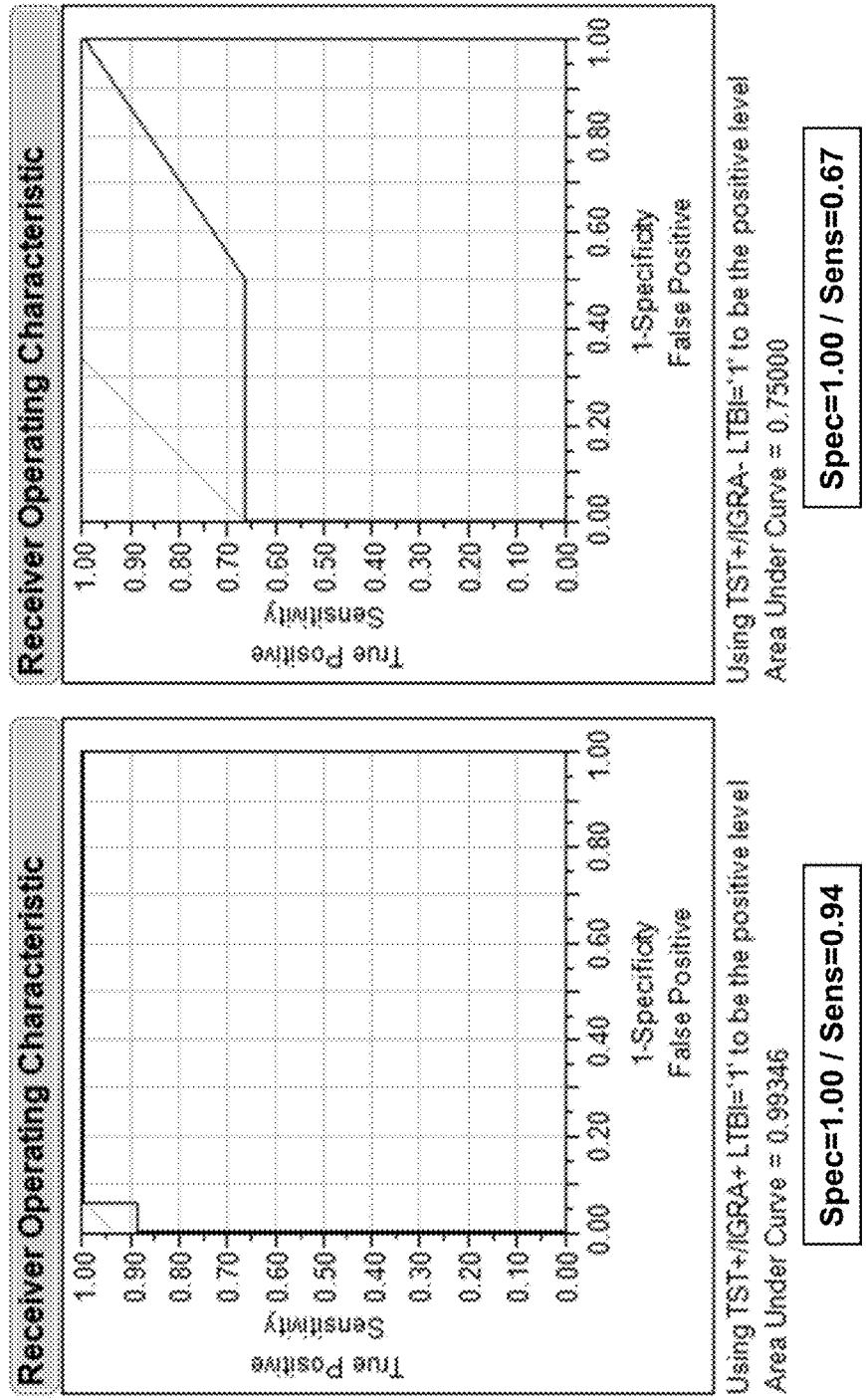
FIG. 19 provides a summary of FACS-TB (PPD) results in CD4$^+$ T-cells from donors vs. TST+/IGRA+ and TST+/IGRA− cases.
Figure 20:
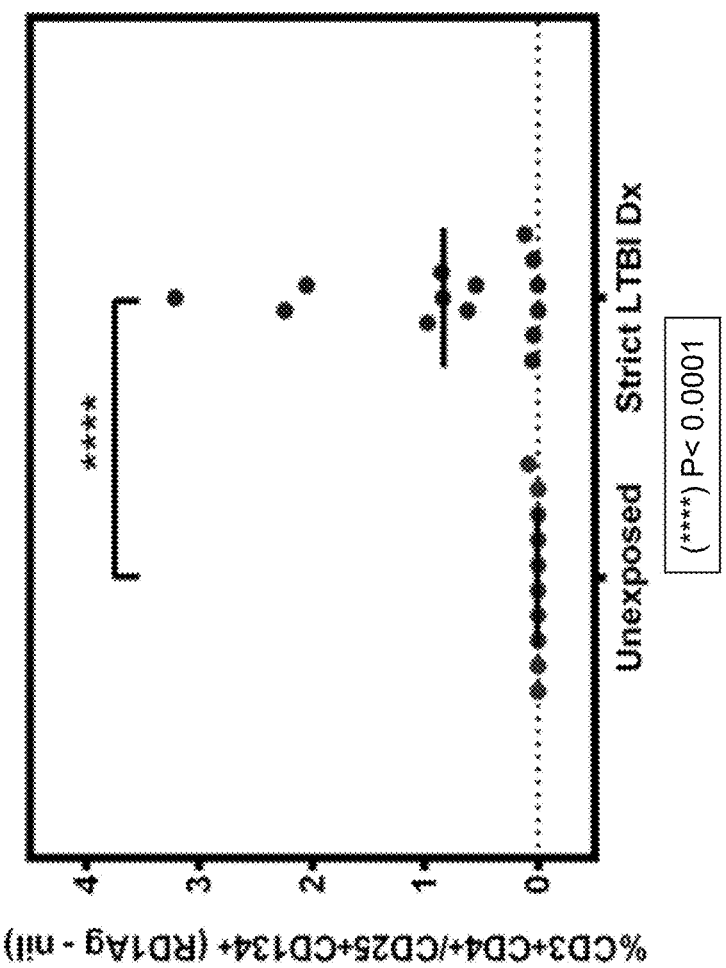
FIG. 20 contains a graph plotting FACS-TB (RD1) results in CD4$^+$ T-cells from unexposed donors (N=10) vs. untreated LTBI cases (N=14). (****) P<0.0001 (Mann-Whitney test). Dx=Diagnosis.
Figure 21:
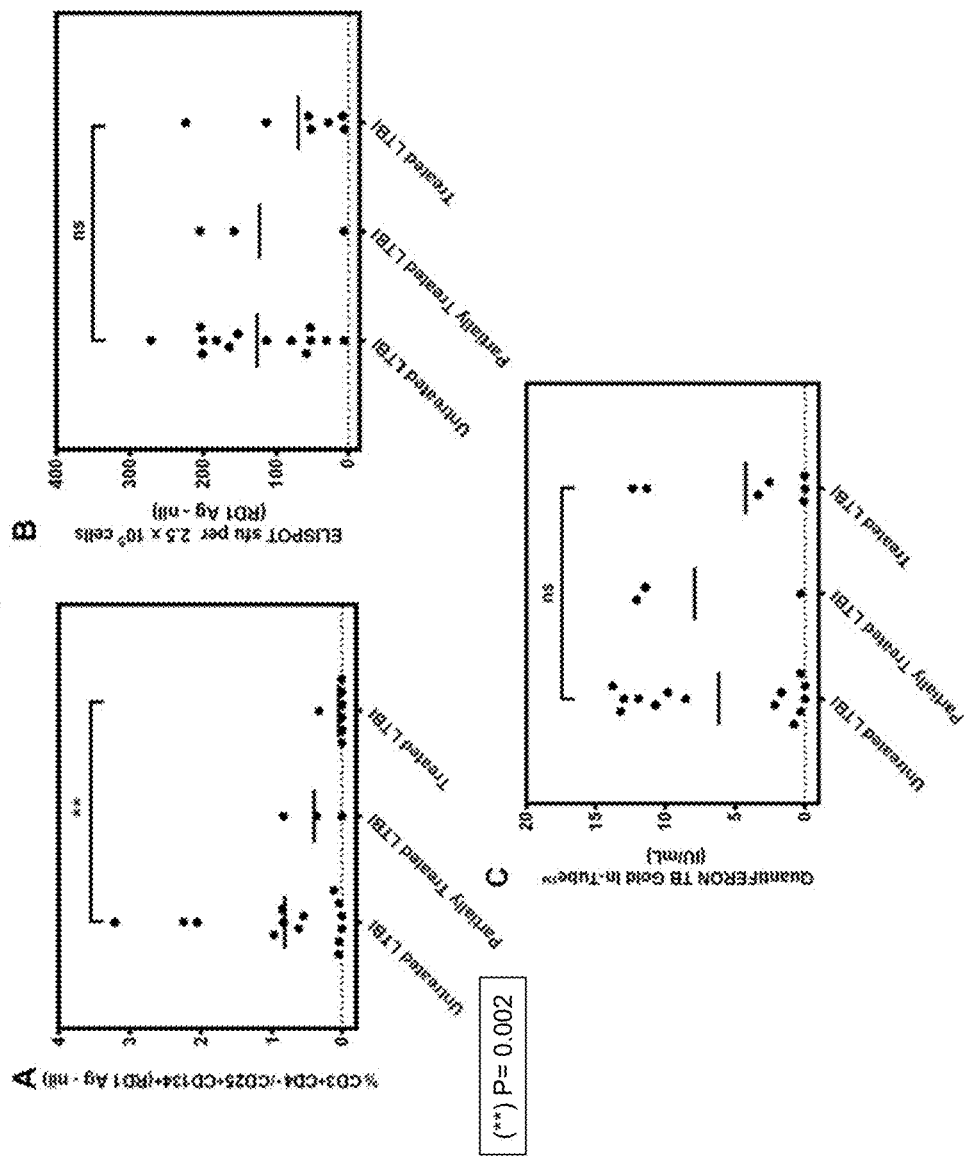
FIGS. 21A-21C contain graphs demonstrating the effect of isoniazid treatment on FACS-TB (CD4+ T-cells; RD1 Ag) (A), TB-ELISPOT (RD1 Ag) (B), and QUANTIFERON-TB GOLD IN-TUBE™ (C) in LTBI cases. (A) LTBI treatment effect on FACS-TB in activated CD4+ T-cells (RD1-Ag-nil). (B) In-house ELISPOT ("TB-ELISPOT") run with the same antigen stimulation conditions; and (C) QUANTIFERON TB GOLD IN-TUBE™; patients had a diagnosis of LTBI with a history of no treatment ("Untreated LTBI"; N=14), partial treatment ("Partially Treated LTBI"; N=3), or full treatment ("Treated LTBI"; N=7). Means (black lines). (**) P=0.002 (Dunn's test). NS=no statistical significant differences. Tx=treatment.

11. Set FACS-TB test gating (% CD25⁺CD134⁺) in activated T-cells (CD3⁺CD4⁺ (or CD8⁺)) (Please see FIGS. 3 and 4). Gate for viable lymphocytes by using side and forward scatter plots in SEAB-stimulated and unstimulated samples. Gate on CD3⁺/CD4⁺; D) % CD3⁺CD4⁺/CD25⁺ CD134⁺ co-expression (right upper quadrant box set from prior step) with SEAB (non-specific T-cell activator; positive control), unstimulated sample (negative or nil control), PPD (non-specific MTB antigen), ESAT-6/CFP-10 peptide mixture (specific MTB antigen of RD1 (region of difference) peptide antigens) and *Candida* (antigen-specific T-cell activator; positive control). Percentages (or numbers) indicate the calculated distribution of CD25⁺ CD134⁺ among CD3⁺ (or CD3⁻)CD4⁺ (or CD8⁺) cells after the subtraction of background (nil).

Thirty-three consecutive subjects, including 17 healthy donors with TST-IGRA-results, 9 patients with TST+/IGRA+ results (8 with probable TB exposure and 1 close contact), 2 with recently diagnosed active TB, 3 patients with TST+/IGRA− results (2 with probable TB exposure and 1 with possible TB exposure), and 2 with remotely treated TB (one with IGRA− results) were analyzed. Statistically significant differences in FACS-TB results were found between healthy donors and suspected LTBI cases (P<0.001). FACS-TB for CD4⁺ T-cells AUC of ROC was 0.97; sensitivity of 100.0% and specificity of 88% at the best cut off of 0.07% of T-cells for clinical diagnosis of LTBI with TST+/IGRA+ results. In addition, an increased number of activated CD8⁺ T-cells with CD25⁺/CD134⁺ co-expression was found not only in a case of disseminated TB but also in a subset of LTBI cases. Additional results are provided in FIGS. 1-19.

The FACS-TB testing of CD4⁺ T-cells revealed a high diagnostic yield for LTBI in this patient population.

Example 2—Treatment Effect of Isoniazid on T-Cell CD25⁺/CD134⁺ Co-Expression in Latent Tuberculosis Infection The following was performed to evaluate flow cytometric detection of antigen-specific activated T-cell CD25⁺CD134⁺ co-expression in highly suspected LTBI subjects with a history of no treatment or treatment with isoniazid. Flow cytometric detection of CD25⁺CD134⁺ co-expression on antigen-stimulated T-cells was performed using peripheral blood mononuclear cells (PBMCs) samples from subjects likely to have LTBI (risk factors for TB and TST+/IGRA+ tests or TST conversion) and having a history of no treatment partial treatment, or complete isoniazid treatment. PBMCs were stimulated with specific (RD1-peptides), non-specific (PPD) MTB antigens, or controls, stained with fluorescent dye-conjugated anti-CD3, anti-CD4, anti-CD25, and anti-OX40 antibodies, and 2×10⁵ cells were analyzed by FACS. The percentages of CD3⁺CD4⁺ T-cells co-expressing CD25 and CD134 in these three populations were compared.

Fourteen highly suspected LTBI subjects naïve to treatment, three subjects partially treated with isoniazid, and nine subjects with prior completion of LTBI therapy were studied. Statistically significant reductions in CD25⁺CD134⁺ co-expression in antigen-stimulated T-cells in patients with prior LTBI treatment (P<0.05) were observed. There were no statistical differences in QUANTIFERON TB GOLD IN-TUBE™ results and an ELISPOT run under the same antigen stimulation conditions. Additional results are provided in FIGS. 20-23.

These results demonstrate that a FACS assay can detect LTBI with reactivation potential. For example, these results demonstrate that an ex vivo FACS method with CD3+CD4+ and CD3+/CD8+ T-cells with either RD1-peptides or PPD antigens have a high diagnostic accuracy to detect suspected LTBI cases, that a FACS method with CD3+CD4+ T-cells with either RD1-peptides or PPD can detect suspected LTBI cases with reactivation potential (e.g., high reactivation potential; reactivatable LTBI), and that a FACS method with CD3+/CD8+ T-cells with PPD antigen can detect suspected LTBI cases with reactivation potential (e.g., high reactivation potential; reactivatable LTBI).

Example 3—Flow Cytometric Approach to Evaluate Innate Immunity in Subjects Exposed to TB with Negative TST and IGRA Results The following was performed to evaluate the flow cytometric detection of CD3⁻CD8⁺CD25⁺CD134⁻ cells in response to MTB antigens in healthy subjects with negative Tuberculin skin test (TST) and Interferon-γ release assay (IGRA) and various likelihood of prior TB exposures. A prospective evaluation of FACS detection of CD3⁻CD8⁺ CD25⁺CD134⁻ cells in response to MTB antigens was performed using peripheral blood mononuclear cells (PBMCs) samples from healthy subjects with unlikely, possible, and probable prior TB exposure and negative TST and IGRA results. PBMCs were stimulated with specific (RD1-peptides) and non-specific (PPD) MTB antigens as well as controls, stained with fluorescent dye-conjugated anti-CD3, anti-CD8, anti-CD25, and anti-OX40 (anti-CD134) antibodies, and 2×10⁵ cells were analyzed by FACS (BD FACSCANTO™). The area under the receiver characteristic (ROC) curve (AUC) was analyzed, and various cut-offs were tested to best differentiate these populations.

Figure 24:
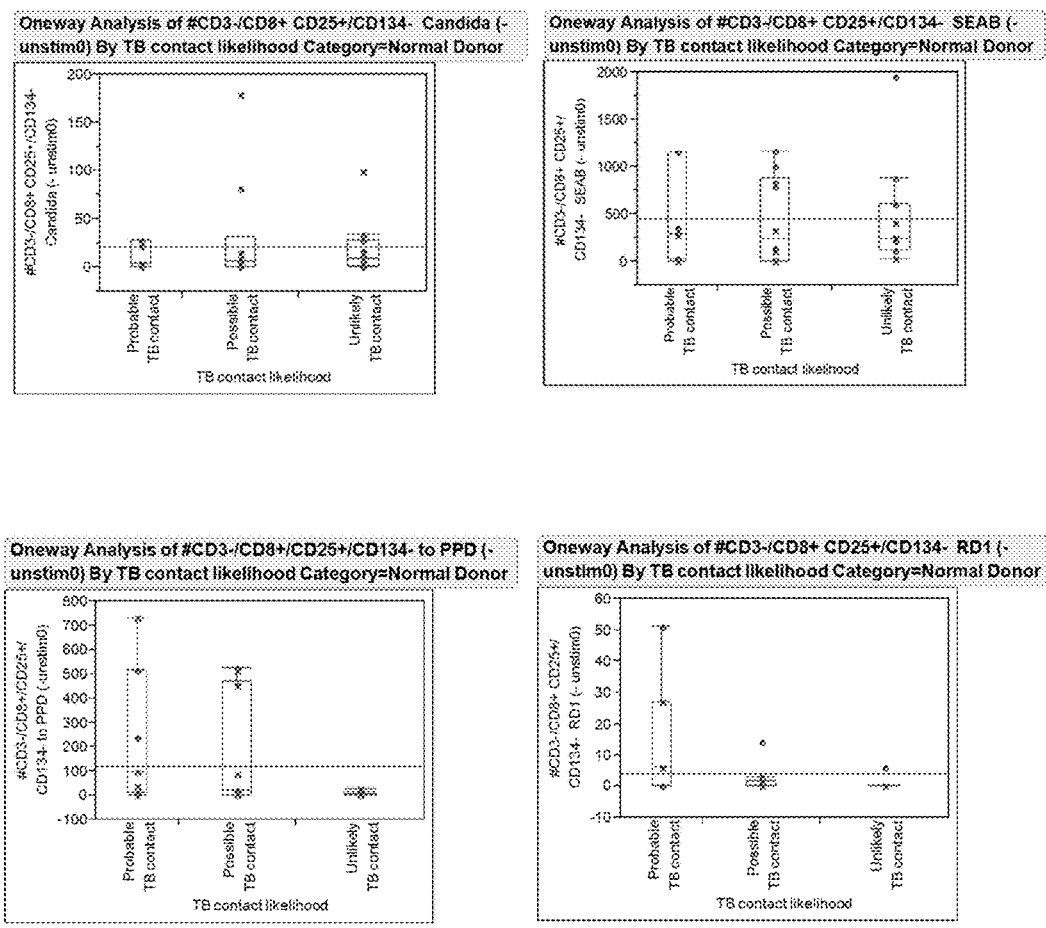
FIG. 24 contains graphs plotting FACS results for $CD3^-CD8^+CD25^+CD134^-$ lymphocyte subsets activated by incubation with *candida* antigen (upper left), SEAB superantigen (upper right), PPD antigen (lower left) and RD1 peptide antigens (lower right) from healthy subjects with probable TB exposure (N=7), possible TB exposure (N=10), or no TB exposure (N=11), who have both negative QUANTIFERON TB GOLD IN-TUBE™ (Cellestis, Australia) and TST results.

Twenty-eight consecutive subjects, including 11 healthy donors born in the US and with unlikely prior TB exposure; 10 subjects with possible TB exposure (being born in and nonmedical trips to moderate to high TB prevalence areas (HTA)), and 7 subjects with prior close contact with active TB patients in HTA and with TST-IGRA− results were analyzed. Statistically significant differences in number of CD3⁻CD8⁺CD25⁺CD134⁻ cells in response to PPD (P=0.017) and RD1-peptide antigens (P=0.028) between subjects with unlikely and probable prior TB exposure were observed (FIG. 24). No significant differences were found in these PBMC subsets stimulated to *candida* and staphylococcal enterotoxin A and B antigens (FIG. 24) with any of these antigens, potentially suggesting a biomarker candidate of innate immunity.

These results suggest that flow cytometric detection of CD3⁻CD8⁺CD25⁺CD134⁻ cells in response to MTB antigens can detect innate immune recall response to prior TB exposures in subjects without adaptive immune response to MTB antigens.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying and treating a latent tuberculosis infection with reactivation potential comprising:
   (a) obtaining a sample comprising human blood cells, wherein said human blood cells are from a human having had a previous TST-positive or IGRA-positive test result,
   (b) exposing said human blood cells to an $M.$ $tuberculosis$ antigen preparation to obtain a stimulated human blood cell preparation,
   (c) contacting said stimulated human blood cell preparation with a fluorescently labeled anti-CD8 antibody, a fluorescently labeled anti-CD25 antibody, and a fluorescently labeled anti-CD134 antibody to obtain a labeled cell preparation,
   (d) introducing said labeled cell preparation into a flow cytometer to determine the percentage of $CD8^+/CD25^-/CD134^+$ cells present within said labeled cell preparation,
   (e) identifying the human as having a latent tuberculosis infection with reactivation potential when the percentage of $CD8^+/CD25^-/CD134^+$ cells present within said labeled cell preparation is greater than 0.11%, and
   (f) treating the human identified as having the latent tuberculosis infection with reactivation potential, wherein said treating step comprises administering isoniazid.

2. The method of claim 1, wherein said human blood cells are human blood cells from a human having had a previous TST-positive and IGRA-positive test result.

3. The method of claim 1, wherein said human blood cells are freshly obtained human blood cells, or are human blood cells that were frozen.

4. The method of claim 1, wherein said human blood cells are human peripheral blood mononuclear cells (PBMCs).

5. The method of claim 1, wherein said $M.$ $tuberculosis$ antigen preparation comprises a polypeptide selected from the group consisting of $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides.

6. The method of claim 1, wherein said $M.$ $tuberculosis$ antigen preparation comprises $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides.

7. The method of claim 1, wherein said method further comprises contacting said stimulated human blood cell preparation with a fluorescently labeled anti-CD4 antibody.

8. The method of claim 7, wherein the percentage of $CD4^+/CD25^-/CD134^+$ cells present within said labeled cell preparation is determined.

* * * * *

UNITED STATES PATENT AND TRADEMARK OFFICE
CERTIFICATE OF CORRECTION

PATENT NO. : 10,401,360 B2
APPLICATION NO. : 14/264286
DATED : September 3, 2019
INVENTOR(S) : Patricio Escalante and Tobias Peikert Page 1 of 1

It is certified that error appears in the above-identified patent and that said Letters Patent is hereby corrected as shown below:

In the Claims

Column 13, Line 32 (Claim 1), please delete "CD25-" and insert -- CD25+ --, therefor;

Column 13, Line 35 approx. (Claim 1), please delete "CD25-" and insert -- CD25+ --, therefor;

Column 14, Line 38 (Claim 8), please delete "CD25-" and insert -- CD25+ --, therefor.

Signed and Sealed this
Twenty-sixth Day of November, 2019

Andrei Iancu
*Director of the United States Patent and Trademark Office*

```
                          SEQUENCE LISTING

<160> NUMBER OF SEQ ID NOS: 6

<210> SEQ ID NO 1
<211> LENGTH: 20
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly
            20

<210> SEQ ID NO 2
<211> LENGTH: 20
<212> TYPE: PRT
<213> ORGANISM: Mycobacterium tuberculosis

<400> SEQUENCE: 2

Glu Gly Lys Gln Ser Leu Thr Lys Leu Ala Ala Ala Trp Gly Gly Ser
1               5                   10                  15

Gly Ser Glu Ala
            20

<210> SEQ ID NO 3
<211> LENGTH: 24
<212> TYPE: PRT
<213> ORGANISM: Mycobacterium tuberculosis

<400> SEQUENCE: 3

Ala Trp Gly Gly Ser Gly Ser Glu Ala Tyr Gln Gly Val Gln Gln Lys
1               5                   10                  15

Trp Asp Ala Thr Ala Thr Glu Leu
            20

<210> SEQ ID NO 4
<211> LENGTH: 20
<212> TYPE: PRT
<213> ORGANISM: Mycobacterium tuberculosis

<400> SEQUENCE: 4

Thr Ala Thr Glu Leu Asn Asn Ala Leu Gln Asn Leu Ala Arg Thr Ile
1               5                   10                  15

Ser Glu Ala Gly
            20

<210> SEQ ID NO 5
<211> LENGTH: 20
<212> TYPE: PRT
<213> ORGANISM: Mycobacterium tuberculosis

<400> SEQUENCE: 5

Ala Gln Ala Ala Val Val Arg Phe Gln Glu Ala Ala Asn Lys Gln Lys
1               5                   10                  15

Gln Glu Leu Asp
            20
```

```
<210> SEQ ID NO 6
<211> LENGTH: 20
<212> TYPE: PRT
<213> ORGANISM: Mycobacterium tuberculosis

<400> SEQUENCE: 6

Glu Ile Ser Thr Asn Ile Arg Gln Ala Gly Val Gln Tyr Ser Arg Ala
1               5                   10                  15

Asp Glu Glu Gln
            20
```